United States Patent [19]

Takagi et al.

[11] Patent Number: 4,720,495
[45] Date of Patent: Jan. 19, 1988

[54] BENZO[IJ]QUINOLIZINE-2-CARBOXYLIC ACIDS USEFUL FOR TREATING BACTERIAL INFECTION

[75] Inventors: Atsushi Takagi; Masao Yajima; Toshiaki Kikuchi, all of Tokyo; Masaki Saeki, Matsudo, all of Japan

[73] Assignee: Tokyo Tanabe Co. Limited, Japan

[21] Appl. No.: 865,530

[22] Filed: May 20, 1986

[30] Foreign Application Priority Data

May 24, 1985 [JP] Japan ................. 60-110226
May 24, 1985 [JP] Japan ................. 60-110227

[51] Int. Cl.$^4$ ............... A61K 31/495; C07D 403/04; C07D 401/04
[52] U.S. Cl. .................. 514/253; 544/361; 546/95; 546/137
[58] Field of Search ............ 544/361; 514/253

[56] References Cited

U.S. PATENT DOCUMENTS

| | | | |
|---|---|---|---|
| 4,014,877 | 3/1977 | Gerster | 546/95 |
| 4,416,884 | 11/1983 | Ishikawa et al. | 544/361 |
| 4,535,161 | 8/1985 | Hayakawa | 544/361 |
| 4,594,347 | 6/1986 | Ishikawa et al. | 544/361 |
| 4,659,734 | 4/1987 | Enomoto et al. | 544/361 |

FOREIGN PATENT DOCUMENTS

| | | | |
|---|---|---|---|
| 5040616 | 3/1980 | Japan | 544/361 |
| 2086905 | 4/1981 | United Kingdom | 546/95 |
| 2091726 | 8/1982 | United Kingdom | 544/361 |

OTHER PUBLICATIONS

Murai et al, CA 97-207669y.
Daiichi Seiyaku Co. Ltd., CA 99-88227g.
Otsuka Pharm. Co. Ltd., CA 99-88225e.
Otsuka Pharm. Co. Ltd., CA 99-93740y.
Morita et al, CA 100-203177u.
Ishikawa et al, CA 104-68763x.
Irikura et al, CA 102-166766g.
Otsuka Pharm. Co. Ltd., CA 103-42641k.

Primary Examiner—Donald G. Daus
Assistant Examiner—Cecilia Shen
Attorney, Agent, or Firm—McGlew and Tuttle

[57] ABSTRACT

Benzo[ij]quinolizine-2-carboxylic acid derivatives of the general formula [I] and the salts, and their hydrates are provided:

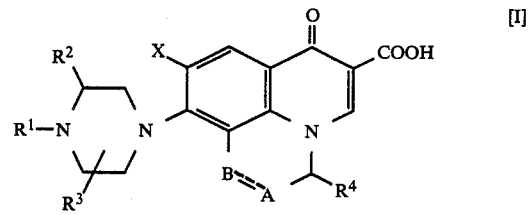

wherein A is a methylene group and B is a carbonyl group when A and B are linked by a single bond, or A and B unite together to form a vinylene group when A and B are linked by a double bond, $R^1$ is a hydrogen atom, a $C_{1-3}$ alkyl group or a 2-hydroxyethyl group, $R^2$ and $R^3$ are hydrogen atoms, methyl groups or ethyl groups and may be identical to or different from each other, $R^3$ may be attached to the same carbon atom as $R^2$, $R^4$ is a methyl or ethyl group, and X is a halogen atom. The benzo[ij]quinolizine-2-carboxylic acid derivatives and the salts, and their hydrates have good adsorbability from the digestive tract into the circulating blood and exhibit excellent and long-lasting antibacterial activity.

19 Claims, No Drawings

BENZO[IJ]QUINOLIZINE-2-CARBOXYLIC ACIDS USEFUL FOR TREATING BACTERIAL INFECTION

BACKGROUND OF THE INVENTION (1) Field of the Invention

This invention relates to benzo[ij]quinolizine-2-carboxylic acid derivatives. More particularly, it relates to 9-halogeno-5-alkyl-8-(unsubstituted to trisubstituted piperazinyl) benzo[ij]quinolizine-2-carboxylic acid derivatives having good absorbability from the digestive tract into the circulating blood and exhibiting long-lasting antibacterial activity.

(2) Description of the Prior Art

In the field of synthetic antibacterial agents, typical examples of well-known compounds having a halogen substituent and containing a pyridonecarboxylic acid structure include 1-ethyl-6-fluoro-1, 4-dihydro-7-(1-piperazinyl)-4-oxoquinoline-3-carboxylic acid (hereinafter referred to as norfloxacin; Japanese Patent Publication No. 34,144/'80), 9-fluoro-3-methyl-10-(4-methyl-1-piperazinyl)-7-oxo-2, 3-dihydro-7H-pyrido[1,2,3-de][1,4]benzoxazine-6-carboxylic acid (hereinafter referred to as ofloxacin; Japanese Patent Laid-Open Nos. 46,986/'82 and 34,968/'85), 9-fluoro-6,7-dihydro-5-methyl-8-(4-methyl-1-piperazinyl)-1-oxo-1H, 5H-benzo[ij]quinolizine-2-carboxylic acid (hereinafter referred to as OPC-7241; Japanese Patent Laid-Open No. 76,875/'80), 9-fluoro-6,7-dihydro-1,7-dioxo-5-methyl-1H, 5H-benzo[ij]quinolizine-2-carboxylic acid (hereinafter referred to as Compound α; Japanese Patent Laid-Open No. 127,099/'76) and the like. (Ofloxacin)

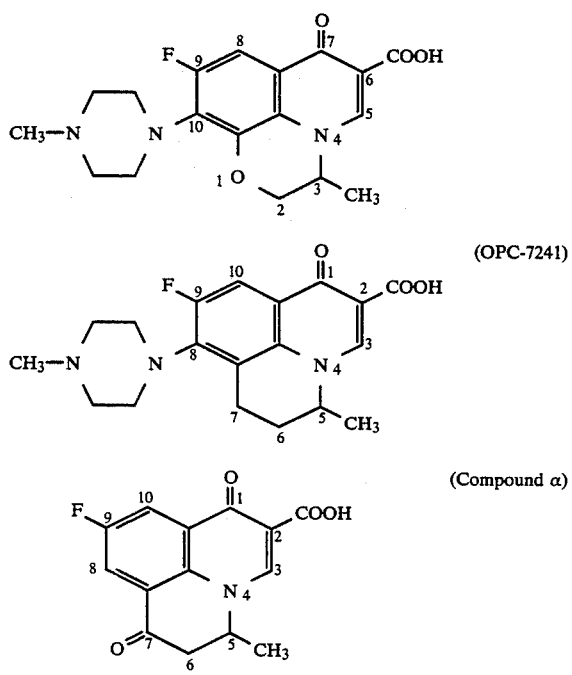

However, it was reported by Murayama et al. (CHEMOTHERAPY, Vol. 29, Supplement No. 4, p. 98, 1981) that, when norfloxacin was administered orally to fasted animals (e.g., mice) in a dose of 50 mg/kg, its degree of absorption into the serum after 30 minutes was expressed by an average peak value of 1±0.6 μg/ml. Moreover, it was discussed by Goto et al. (CHEMOTHERAPY, Vol. 32, Supplement No. 1, p. 22, 1984) that norfloxacin exhibited excellent antibacterial activity when evaluated by in vitro tests with Gram-negative and Gram-positive bacteria, but it was somewhat disadvantageous in enteral absorbability.

Thus, recent studies of synthetic antibacterial agents containing a pyridonecarboxylic acid structure have come to focus attention on their bioavailability (the degree of biological utilizability) in case of oral administration, rather than on their relative superiority in antibacterial activity, provided that they have at least a certain level of activity. In the course of such studies, ofloxacin and OPC-7241 were developed. It was reported by Goto et al. (CHEMOTHERAPY, Vol. 32, Supplement No. 1, p. 22, 1984) that, when ofloxacin was administered orally to fasted mice in a dose of 1 mg/mouse (equivalent to 50 mg/kg body weight), its serum concentration reached 10 μg/ml after 30 minutes, indicating an increase in enteral absorbability over norfloxacin. From the viewpoint of bioavailability, however, enteral absorbability still leaves room for improvement. In addition, it was also described in the same report that, 2 hours after administration, its residual concentration in the serum decreased to 1.5 μg/ml. This indicates the necessity of developing a technique for prolonging the duration of action of such drugs.

As for OPC-7241, it was presented in the lecture given at the Fifth Medicinal Chemistry Symposium (Kyoto; Dec. 9-10, 1984) on the subject of "Structures and Antibacterial Activities of Pyrido[1,2,3-de]-1, 4-benzoxazine-6-carboxylic acid-related Compounds" that its enteral absorbability was almost equal to that of ofloxacin. Accordingly, it may be expected that OPC-7241 involves the same problems as described in connection with ofloxacin.

On the other hand, Compound α has only been reported to be useful as an intermediate material for the preparation of 9-fluoro-6, 7-dihydro-7-hydroxy-5-methyl-1-oxo-1H, 5H-benzo[ij]quinolizine-2-carboxylic acid (Japanese Patent Laid-Open No. 127,099/'76), and no detailed report on its antibacterial activity has been published. When the present inventors conducted a confirmatory experiment on the antibacterial activity of Compound α, it was found that its efficacy against Gram-positive bacteria was low and, moreover, it was utterly ineffective against Gram-negative bacteria (such as Pseudomonas aeruginosa, Serratia marcescens and the like) to which great importance has recently been attached especially in the field of bacterial infection.

SUMMARY OF THE INVENTION

As a result of comparative studies on a variety of novel compounds having a halogen substituent in the molecule and containing a pyridonecarboxylic acid structure, the present inventors have discovered that the compounds obtained by converting the oxymethylene group (—O—CH₂—) in the 1-2 position of ofloxacin or the ethylene group (—CH₂—CH₂—) in the 7-6 position of OPC-7241 into a carbonylmethylene group

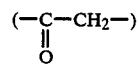

or a vinylene group (—CH=CH—) exhibit excellent antibacterial activity and, moreover, have better enteral absorbability and a longer duration of action than ofloxacin and OPC-7241. The present invention has been completed on the basis of this discovery.

According to the present invention, there is provided a benzo[ij]quinolizine-2-carboxylic acid derivative of the following general formula [I]:

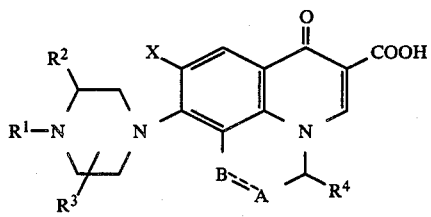

wherein A is a methylene group and B is a carbonyl group when A and B are linked by a single bond, or A and B unite together to form a vinylene group when A and B are linked by a double bond, $R^1$ is a hydrogen atom, an alkyl group of 1 to 3 carbon atoms or a 2-hydroxyethyl group, $R^2$ and $R^3$ are hydrogen atoms, methyl groups or ethyl groups and may be identical to or different from each other, $R^3$ may be attached to the same carbon atom as $R^2$, $R^4$ is a methyl or ethyl group, and X is a halogen atom.

The benzo[ij]quinolizine-2-carboxylic acid derivatives represented by the above general formula [I] (hereinafter referred to briefly as the present compounds [I]) also comprehend hydrates thereof, as well as physiologically acceptable salts thereof including, for example, salts formed by reaction with inorganic acids (such as hydrochloric acid and sulfuric acid) or organic acids (such as methane-sulfonic acid), salts formed by reaction with metals (such as sodium, potassium, calcium and magnesium) or organic bases, and hydrates of such salts.

DESCRIPTION OF THE PREFERRED EMBODIMENTS (Methods for the Preparation of the Present Compounds [I])

The present compounds [I] can be prepared by hydrolyzing a benzo[ij]quinolizine-2-carboxylic acid ester derivative of the following general formula [II]:

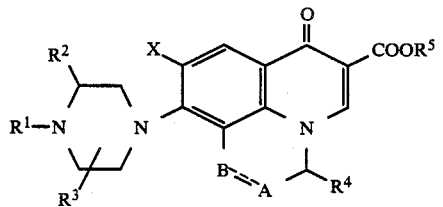

wherein A, B and the type of bond between A and B, as well as $R^1$, $R^2$, $R^3$ and x $R^4$, are as previously defined, and R5 is a methyl, ethyl or n-propyl group. This method will hereinafter be referred to as Method 1.

This hydrolysis is carried out by treating the benzo[ij]quinolizine-2-carboxylic acid ester derivative [II] with an acid or alkali in water, methanol, ethanol, n-propanol, acetic acid or a mixture of two or more such solvents, for a period of time ranging from 30 minutes to 48 hours and preferably from 1 to 24 hours. The reaction temperature should be in the range of 30° to 150° C., preferably 60° to 130° C., when an acid is used, and in the range of 0° to 100° C., preferably 0° to 50° C., when an alkali is used. Useful acids include, for example, hydrochloric acid, sulfuric acid and the like. Useful alkalis include, for example, 0.1 to 5N, preferably 0.5 to 3N, aqueuos solutions of sodium hydroxide or potassium hydroxide. Both the acid and the alkali should be used in excess relative to the benzo[ij]quinolizine-2-carboxylic acid ester derivative [II].

The present compounds [I] can also be prepared by the nucleophilic substitution reaction of a carboxylic acid derivative of the following general formula [III]:

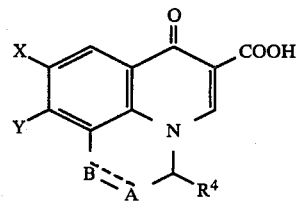

wherein A, B and the type of bond between A and B, as well as $R^4$, and x are as previously defined, and Y is a fluorine or chlorine atom, with a piperazine derivative of the following general formula [IV]:

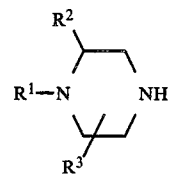

wherein $R^1$, $R^2$ and $R^3$ are as previously defined. This method will hereinafter be referred to as Method 2.

This nucleophilic substitution reaction is carried out, in the absence of solvent or in the presence of a suitable polar solvent, at a temperature of 0° to 200° C., preferably 30° to 150° C., for a period of time ranging from 1 to 48 hours. Suitable polar solvents include, for example, water, ethanol, n-propanol, n-butanol, methyl cellosolve, ethyl cellosolve, pyridine, N,N-dimethylformamide, dimethyl sulfoxide and hexamethylphosphorotriamide, as well as mixtures of two or more such solvents. The molar ratio of the reactants should be such that the piperazine derivative [IV] is used in an amount of 1 to 8 moles, preferably 2 to 5 moles, per mole of the carboxylic acid derivative [III].

The present compounds [I] prepared in the above-described manner may be converted into hydrates according to conventional procedure, or converted into inorganic or organic acid salts, metallic or organic base salts, or hydrates of such salts according to conventional procedure, for example, by reaction with such acids as hydrochloric acid, sulfuric acid and methane-sulfonic acid or such alkalis as sodium hydroxide and potassium hydroxide.

(Methods for the Preparation of Starting Materials Used to Prepare the Present Compounds [I])

Among the benzo[ij]quinolizine-2-carboxylic acid ester derivatives [II] which can be used as the starting material in the above-described Method 1, the compounds in which A is a methylene group, B is a carbonyl group, and A and B are linked by a single bond, i.e. the compounds of the following general formula [V]:

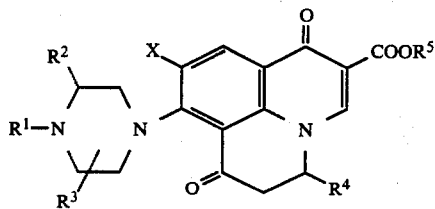

wherein $R^1$, $R^2$, $R^3$, $R^4$, $R^5$ and X are as previously defined, can be prepared by the nucleophilic substitution reaction of a compound of the following general formula [VI]:

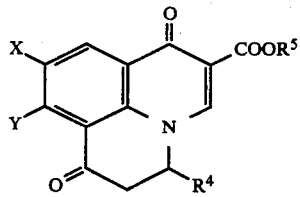

wherein $R^4$, $R^5$, X and Y are as previously defined, with the aforesaid piperazine derivative [IV] (hereinafter referred to as Step a).

This nucleophilic substitution reaction is carried out, in the absence of solvent or in the presence of a suitable reaction solvent, at a temperature of 0° to 200° C., preferably 0° to 100° C., for a period of time ranging from 1 to 48 hours. Suitable reaction solvents are the solvents capable of dissolving the resulting compound [V] and include, for example, benzene, chloroform, dichloromethane, ethyl acetate, acetonitrile, ethanol, n-propanol, n-butanol, N,N-dimethylformamide, dimethyl sulfoxide and hexamethylphosphorotriamide, as well as mixtures of two or more such solvents. The molar ratio of the reactants should be such that the piperazine derivative [IV] is used in an amount of 1 to 8 moles, preferably 2 to 5 moles, per mole of the compound [VI].

Among the benzo[ij]quinolizine-2-carboxylic acid ester derivatives [II], the compounds in which A and B unite together to form a vinylene group, and A and B are linked by a double bond, i.e. the compounds of the following general formula [VII]:

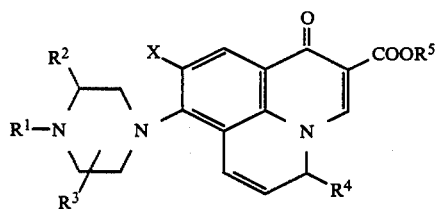

wherein $R^1$, $R^2$, $R^3$, $R^4$, $R^5$ and X are as previously defined, can be prepared by selectively reducing the compound [V] obtained by the aforesaid Step a to a compound of the following general formula [VIII]:

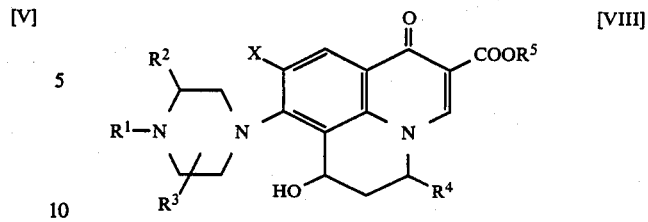

wherein $R^1$, $R^2$, $R^3$, $R^4$, $R^5$ and X are as previously defined, (hereinafter referred to as Step b) and then subjecting this compound to intramolecular dehydration (hereinafter referred to as Step c).

The selective reduction in Step b is carried out by reacting the compound [V] with sodium borohydride in water, methanol, ethanol, n-propanol, isopropanol or a mixture of two or more such solvents. The reaction temperature may suitably be in the range of 0° to 50° C., and the reaction time may suitably be in the range of 1 to 10 hours. Sodium borohydride is used in an amount of 0.25 to 4 moles per mole of the compound [V]. If the compound [VIII] obtained by this selective reduction is hydrolyzed with a suitable acid or alkali, there may be obtained a 9-halogeno-5-alkyl-8-(unsubstituted to trisubstituted piperazinyl)-7-hydroxy-6,7-dihydro-1-oxo-1H,5H-benzo[ij]quinolizine-2-carboxylic acid derivative having excellent antimicrobial activity and represented by the following general formula [IX]:

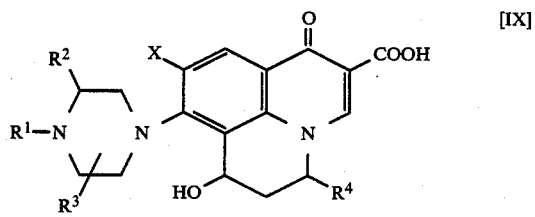

wherein $R^1$, $R^2$, $R^3$, $R^4$ and X are as previously defined.

The intramolecular dehydration in Step c is carried out by reacting the compound [VIII] with a dehydrating agent, in the absence of solvent or in the presence of a suitable reaction solvent, at a temperature of 0° to 100° C. for a period of time ranging from 1 to 48 hours. Useful dehydrating agents include, for example, such acids as hydrochloric acid, sulfuric acid, polyphosphoric acid, polyphosphoric acid ester, acetic acid, toluenesulfonic acid and the like. Among them, polyphosphoric acid and polyphosphoric acid ester are preferred. Suitable reaction solvents include, for example, water, benzene, chloroform, methanol, ethanol, n-propanol and isopropanol. The dehydrating agent is used in excess relative to the compound [VIII].

Among the carboxylic acid derivatives [III] which can be used as one of the starting materials in the above-described Method 2, the compounds in which A is a methylene group, B is a carbonyl group, and A and B are linked by a single bond, i.e. the compounds of the following general formula [X]:

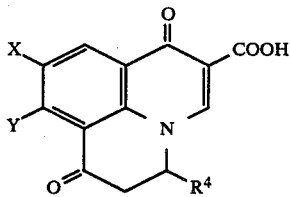

wherein R⁴, X and Y are as previously defined, can be prepared by hydrolyzing the aforesaid compound [VI] (hereinafter referred to as Step d).

This hydrolysis is carried out by treating the compound [VI] with an excess of a mineral acid (such as hydrochloric acid or sulfuric acid) in water, methanol, ethanol, n-propanol, acetic acid or a mixture of two or more such solvents, for a period of time ranging from 30 minutes to 48 hours and preferably from 1 to 5 hours. The reaction temperature should be in the range of 30° to 150° C. and preferably 60° to 130° C.

Among the carboxylic acid derivatives [III], the compounds in which A and B unite together to form a vinylene group, and A and B are linked by a double bond, i.e. the compounds of the following general formula [XI]:

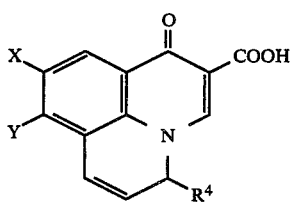

wherein R⁴, X and Y are as previously defined, can be prepared by selectively reducing the compound [X] obtained by the aforesaid Step d to a compound of the following general formula [XII]:

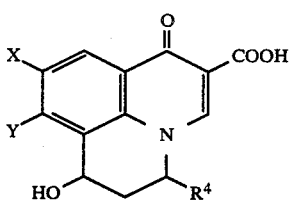

wherein R⁴, X and Y are as previously defined, (hereinafter referred to as Step e) and then subjecting this compound to intramolecular dehydration (hereinafter referred to as Step f).

The selective reduction in Step e and the intramolecular dehydration in Step f may be carried out under the same conditions as described above for the selective reduction in Step b and the intramolecular dehydration in Step c.

The compound [VI] used as one of the starting materials in Step a or Step d can be prepared by reacting an aniline derivative of the following general formula [XIII]:

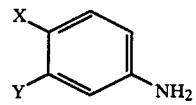

wherein X and Y are as previously defined, with a β-lactone derivative of the following general formula [XIV]:

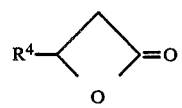

wherein R⁴ is as previously defined, to form a compound of the following general formula [XV]:

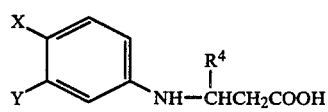

wherein R⁴, X and Y are as previously defined, (hereinafter referred to as Step g); cyclocondensing the compound [XV] to form a compound of the following general formula [XVI]:

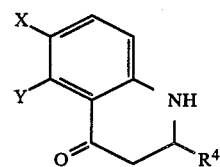

wherein R⁴, X and Y are as previously defined, (hereinafter referred to as Step h); reacting the compound [XVI] with a malonic ester derivative of the following general formula [XVII]:

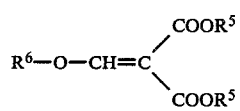

wherein $R^5$ is as previously defined and $R^6$ is a methyl or ethyl group, to form a compound of the following general formula [XVIII]:

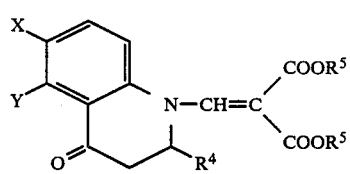

wherein R⁴, R⁵, X and Y are as previously defined, (hereinafter referred to as Step j); and finally cyclocondensing the compound [XVIII] to obtain the desired compound [VI] (hereinafter referred to as Step k).

The reaction in Step g is carried out, in the absence of solvent or in the presence of water, ethanol, n-propanol, isopropanol, acetic acid, acetonitrile, N,N-dimethylformamide or dimethyl sulfoxide, at a temperature of 70° to 130° C. for a period of time ranging from 30 minutes to 5 hours. The molar ratio of the reactants should be such that the β-lactone derivative [XIV] is used in an amount of 1 to 1.5 moles per mole of the aniline derivative [XIII].

The reaction in Step j is carried out, in the absence of solvent or in the presence of benzene, toluene,n-butanol, N,N-dimethylformamide or dimethyl sulfoxide, at a temperature of 150° to 250° C. for a period of time ranging from 30 minutes to 5 hours. The molar ratio of the reactants should be such that the malonic ester derivative [XVII] is used in an amount of 1 to 3 moles per mole of the compound [XVI].

The cyclocondensation reactions in Step h and Step k are carried out at a temperature of 50° to 200° C. by using polyphosphoric acid, polyphosphoric acid ester or sulfuric acid as a condensing agent. The condensing agent is used in an amount equaling 2 to 50 times the weight of the compound [XV] in Step h or the compound [XVIII] in Step k. The reaction time may suitably range from 1 to 48 hours in Step h and from 10 minutes to 24 hours in Step k.

(In Vitro Antibacterial Activity)

The in vitro antibacterial activities of typical examples of the present compounds [I] were evaluated in terms of the minimal inhibitory concentration defined as the lowest concentration of the compound preventing the bacterial growth. The Gram-positive bacteria used as test microorganisms included *Bacillus subtilis, Staphylococcus aureus* and *Streptococcus faecalis*, and the Gram-negative bacteria used as test microorganisms included *Escherichia coli, Enterobacter cloacae, Klebsiella pneumoniae, Proteus vulgaris, Pseudomonas aeruginosa, Serratia marcescens* and *Salmonella enteritidis*. The minimal inhibitory concentration (cultured at 37° C. for 20 hours) was determined according to the standard method prescribed by the Japan Society of Chemotherapy (CHEMOTHERAPY, Vol. 29, No. 1, p. 76, 1981). The following compounds were used as typical examples of the present compounds [I]. At the end of the chemical name of each compound, its tentative designation is given in Parentheses.

9-Fluoro-5-methyl-8-(1-piperazinyl)-6, 7-dihydro-1, 7-dioxo-1H,5H-benzo[ij]quinolizine-2-carboxylic acid (Compound 1);
9-Chloro-5-methyl-8-(1-piperazinyl)-6, 7-dihydro-1, 7-dioxo-1H,5H-benzo[ij]quinolizine-2-carboxylic acid (Compound 2);
9-Fluoro-5-methyl-8-(4-methyl-1-piperazinyl)-6, 7-dihydro-1,7-dioxo-1H, 5H-benzo[ij]quinolizine-2-carboxylic acid (Compound 3);
9-Fluoro-5-ethyl-8-(4-methyl-1-piperazinyl) -6, 7-dihydro-1,7-dioxo-1H, 5H-benzo[ij]quinolizine-2-carboxylic acid (Compound 6);
9-Chloro-5-methyl-8-(4-methyl-1-piperazinyl)-6, 7-dihydro-1,7-dioxo-1H, 5H-benzo[ij]quinolizine-2-carboxylic acid (Compound 7);
9-Fluoro-5-methyl-8-(4-n-propyl-1-piperazinyl)-6, 7-dihydro-1,7-dioxo-1H, 5H-benzo[ij]quinolizine-2-carboxylic acid (Compound 8);
9-Chloro-5-methyl-8-(4-ethyl-1-piperazinyl) -6, 7-dihydro-1, 7-dioxo-1H, 5H-benzo[ij]quinolizine-2-carboxylic acid (Compound 9);
9-Fluoro-5-methyl-8-(3, 5-dimethyl-1-piperazinyl) -6, 7-dihydro-1, 7-dioxo-1H, 5H-benzo[ij]quinolizine-2-carboxylic acid (Compound 11);
9-Fluoro-5-methyl-8-[4-(2-hydroxyethyl) -1-piperazinyl]-6, 7-dihydro-1, 7-dioxo-1H, 5H-benzo[ij]quinolizine-2-carboxylic acid (Compound 12);
9-Fluoro-5-methyl-8-(3, 3-dimethyl-1-piperazinyl) -6, 7-dihydro-1, 7-dioxo-1H, 5H-benzo[ij]quinolizine-2-carboxylic acid (Compound 15);
9-Fluoro-5-methyl-8-3-methyl-1-piperazinyl) -6, 7-dihydro-1, 7-dioxo-1H, 5H-benzo[ij]quinolizine-2-carboxylic acid (Compound 16);
9-Chloro-5-methyl-8-(3, 4, 5-trimethyl-1-piperazinyl) -6, 7-dihydro-1, 7-dioxo-1H, 5H-benzo[ij]quinolizine-2-carboxylic acid (Compound 18);
9-Fluoro-5-methyl-8-(4-methyl-1-piperazinyl) -1-oxo-1H, 5H-benzo[ij]quinolizine-2-carboxylic acid (Compound 19);
9-Fluoro-5-methyl-8-(1-piperazinyl) -1-oxo-1H, 5H-benzo[ij]quinolizine-2-carboxylic acid (Compound 20);
9-Chloro-5-methyl-8-(1-piperazinyl) -1-oxo-1H, 5H-benzo[ij]quinolizine-2-carboxylic acid (Compound 24);
9-Chloro-5-methyl-8-(4-methyl-1-piperazinyl) -1-oxo-1H, 5H-benzo[ij]quinolizine-2-carboxylic acid (Compound 24);
9-Fluoro-5-methyl-8-(3, 4-dimethyl-1-piperazinyl) -1-oxo-1H, 5H-benzo[ij]quinolizine-2-carboxylic acid (Compound 25);
9-Fluoro-5-methyl-8-(3, 3-dimethyl-1-piperazinyl) -1-oxo-1H, 5H-benzo[ij]quinolizine-2-carboxylic acid (Compound 26);
9-Fluoro-5-methyl-8-(3, 4, 5-trimethyl-1-piperazinyl) -1-oxo-1H, 5H-benzo[ij]quinolizine-2-carboxylic acid (Compound 27);
9-Fluoro-5-methyl-8-(3-methyl-1-piperazinyl) -1-oxo-1H, 5H-benzo[ij]quinolizine-2-carboxylic acid (Compound 29);
9-Chloro-5-methyl-8-(3-methyl-1-piperazinyl) -1-oxo-1H, 5H-benzo[ij]quinolizine-2-carboxylic acid (Compound 31);
9-Fluoro-5-ethyl-8-(3-methyl-1-piperazinyl) -1-oxo-1H, 5H-benzo[ij]quinolizine-2-carboxylic acid (Compound 32);
9-Fluoro-5-methyl-8-(4-methyl-1-piperazinyl) -6, 7-dihydro-1,7-dioxo-1H, 5H-benzo[ij]quinolizine-2-carboxylic acid hydrochloride monohydrate (Compound 35);
9-Fluoro-5-methyl-8- (4-methyl-1-piperazinyl) -1-oxo-1H, 5H-benzo[ij]quinolizine-2-carboxylic acid hydrochloride (Compound 37);
9-Fluoro-5-methyl-8- (3, 4-dimethyl-1-piperazinyl) -6, 7-dihydro-1, 7-dioxo-1H, 5H-benzo[ij]quinolizine-2-carboxlyic acid hydrochloride monohydrate (Compound 38);
9-Fluoro-5-methyl-8-(3, 4, 5-trimethyl-1-piperazinyl) -6,7-dihydro-1, 7-dioxo-1H, 5H-benzo[ij]quinolizine-2-carboxylic acid hydrochloride monohydrate (Compound 39).

The test results thus obtained are shown in Table 1. For purposes of comparison, the in vitro antibacterial activities of ofloxacin, OPC-7241 and compound α were evaluated according to the same method as described above and the test results thus obtained are also shown in Table 1.

TABLE 1

| Test microorganism | Minimal inhibitory concentration (μg/ml) | | | | | |
|---|---|---|---|---|---|---|
| | Compound 1 | Compound 2 | Compound 3 | Compound 6 | Compound 7 | Compound 8 |
| *Bacillus subtilis* ATCC 6633 | 0.39 | 0.39 | 0.10 | 0.39 | 0.10 | 0.39 |
| *Staphylococcus aureus* FDA 209P JC-1 | 0.20 | 0.39 | 0.39 | | 0.39 | 0.78 |
| *Streptococcus faecalis* AHU 1085 | 1.56 | | 0.78 | | 1.56 | 3.13 |
| *Escherichia coli* CI-304 | 0.10 | 0.20 | 0.10 | 0.39 | 0.10 | 0.20 |
| *Escherichia coli* NIHJ JC-2 | 0.39 | 0.39 | 0.20 | 0.78 | 0.10 | 0.39 |
| *Enterobacter cloacae* 963 | 0.78 | 0.78 | 0.20 | 0.78 | 0.20 | 0.78 |
| *Klebsiella pneumoniae* PCI 602 | 0.10 | 0.10 | 0.10 | 0.20 | 0.10 | 0.10 |
| *Proteus vulgaris* ATCC 13315 | 0.20 | 0.10 | 0.20 | | 0.10 | |
| *Pseudomonas aeruginosa* NCTC 10490 | 1.56 | 0.78 | 0.78 | | 0.78 | 1.56 |
| *Serratia marcescens* IAM 1184 | 3.13 | | 1.56 | | 3.13 | |
| *Salmonella enteritidis* G14 | 0.39 | | 0.78 | | 0.78 | |

| Test microorganism | Minimal inhibitory concentration (μg/ml) | | | | | |
|---|---|---|---|---|---|---|
| | Compound 9 | Compound 11 | Compound 12 | Compound 15 | Compound 16 | Compound 18 |
| *Bacillus subtilis* ATCC 6633 | 0.20 | 0.10 | | 0.39 | 0.20 | |
| *Staphylococcus aureus* FDA 209P JC-1 | 0.39 | 0.78 | | 0.39 | 0.20 | |
| *Streptococcus faecalis* AHU 1085 | 1.56 | 3.13 | | 3.13 | 0.78 | |
| *Escherichia coli* CI-304 | 0.10 | 0.10 | 0.39 | 0.10 | 0.10 | 0.20 |
| *Escherichia coli* NIHJ JC-2 | 0.20 | 0.20 | | 0.39 | 0.20 | 0.78 |
| *Enterobacter cloacae* 963 | 0.20 | 0.20 | | 0.39 | 0.20 | 0.78 |
| *Klebsiella pneumoniae* PCI 602 | 0.10 | 0.10 | 0.10 | 0.10 | 0.10 | 0.10 |
| *Proteus vulgaris* ATCC 13315 | 0.20 | 0.39 | | | 0.20 | |
| *Pseudomonas aeruginosa* NCTC 10490 | 0.78 | 1.56 | | 3.13 | 0.78 | |
| *Serratia marcescens* IAM 1184 | 3.13 | 3.13 | | | 1.56 | |
| *Salmonella enteritidis* G14 | 0.78 | 0.78 | | 0.78 | 0.78 | |

| Test microorganism | Minimal inhibitory concentration (μg/ml) | | | | | |
|---|---|---|---|---|---|---|
| | Compound 19 | Compound 20 | Compound 22 | Compound 24 | Compound 25 | Compound 26 |
| *Bacillus subtilis* ATCC 6633 | 0.10 | | 0.10 | 0.20 | 0.20 | |
| *Staphylococcus aureus* FDA 209P JC-1 | 0.39 | 0.78 | 0.20 | 0.20 | 0.20 | |
| *Streptococcus faecalis* AHU 1085 | 1.56 | | 0.78 | 0.78 | | |
| *Escherichia coli* CI-304 | 0.20 | 0.20 | 0.10 | 0.20 | 0.20 | 0.20 |
| *Escherichia coli* NIHJ JC-2 | 0.39 | 0.39 | 0.20 | 0.39 | 0.39 | 0.39 |
| *Enterobacter cloacae* 963 | 0.78 | 0.78 | 0.20 | 0.20 | 0.20 | 0.39 |
| *Klebsiella pneumoniae* PCI 602 | 0.10 | 0.20 | 0.10 | 0.10 | 0.10 | 0.20 |
| *Proteus vulgaris* ATCC 13315 | 0.10 | 0.20 | 0.10 | 0.10 | 0.10 | 0.10 |
| *Pseudomonas aeruginosa* NCTC 10490 | 0.78 | 3.13 | 0.78 | 1.56 | 1.56 | 1.56 |
| *Serratia marcescens* IAM 1184 | 1.56 | 3.13 | 0.78 | 1.56 | 1.56 | |
| *Salmonella enteritidis* G14 | 0.78 | 0.78 | 0.78 | 1.56 | 1.56 | 1.56 |

| Test microorganism | Minimal inhibitory concentration (μg/ml) | | | | | |
|---|---|---|---|---|---|---|
| | Compound 27 | Compound 29 | Compound 31 | Compound 32 | Compound 35 | Compound 37 |
| *Bacillus subtilis* ATCC 6633 | | 0.20 | 0.20 | | 0.10 | 0.10 |
| *Staphylococcus aureus* FDA 209P JC-1 | 0.78 | 0.20 | 0.20 | | 0.39 | 0.39 |
| *Streptococcus faecalis* AHU 1085 | | 0.78 | 0.78 | | 0.78 | 1.56 |
| *Escherichia coli* CI-304 | 0.20 | 0.10 | 0.20 | 0.20 | 0.10 | 0.20 |
| *Escherichia coli* NIHJ JC-2 | | 0.10 | 0.10 | 0.39 | 0.20 | 0.39 |
| *Enterobacter cloacae* 963 | 0.39 | 0.20 | 0.20 | 0.78 | 0.20 | 0.78 |
| *Klebsiella pneumoniae* PCI 602 | 0.20 | 0.10 | 0.10 | 0.20 | 0.10 | 0.10 |
| *Proteus vulgaris* ATCC 13315 | 0.10 | 0.10 | 0.10 | | 0.20 | 0.10 |
| *Pseudomonas aeruginosa* NCTC 10490 | | 1.56 | 1.56 | | 0.78 | 0.78 |
| *Serratia marcescens* IAM 1184 | 1.56 | 0.78 | 1.56 | | 1.56 | 1.56 |
| *Salmonella enteritidis* G14 | 0.78 | 0.78 | 1.56 | | 0.78 | 0.78 |

| Test microorganism | Minimal inhibitory concentration (μg/ml) | | | | |
|---|---|---|---|---|---|
| | Compound 38 | Compound 39 | Ofloxacin | OPC-7241 | Compound α |
| *Bacillus subtilis* ATCC 6633 | 0.10 | 0.20 | 0.10 | 0.10 | 12.5 |
| *Staphylococcus aureus* FDA 209P JC-1 | 0.78 | 0.39 | 0.20 | 0.39 | >100 |
| *Streptococcus faecalis* AHU 1085 | 0.78 | 0.78 | 0.78 | 0.78 | >100 |
| *Escherichia coli* CI-304 | 0.10 | 0.20 | 0.10 | 0.20 | 12.5 |
| *Escherichia coli* NIHJ JC-2 | 0.20 | 0.39 | 0.20 | 0.39 | 25 |
| *Enterobacter cloacae* 963 | 0.20 | 0.39 | 0.20 | 0.78 | 12.5 |
| *Klebsiella pneumoniae* PCI 602 | 0.10 | 0.10 | 0.10 | 0.10 | 12.5 |
| *Proteus vulgaris* ATCC 13315 | 0.10 | 0.20 | 0.10 | 0.10 | 25 |
| *Pseudomonas aeruginosa* NCTC 10490 | 1.56 | 3.13 | 0.78 | 3.13 | >100 |
| *Serratia marcescens* IAM 1184 | 1.56 | 1.56 | 0.78 | 1.56 | >100 |
| *Salmonella enteritidis* G14 | 0.78 | 0.78 | 0.39 | 0.78 | 50 |

As is evident from Table 1, it is noted that the present compounds [I] exhibit excellent antibacterial activities which cannot be predicted from the activity of Compound α (having the same fundamental skeleton), and their antibacterial activities bear comparison with those of ofloxacin and OPC-7241.

(Enteral Absorbability)

Using male ICR mice fasted overnight (weighing 20±1 g), the enteral absorbability of some typical examples of the present compounds [I] was tested. This test was carried out by administering 50 mg/kg of each test compound orally to mice and determining its serum concentration 30 minutes, 1 hour, 2 hours and 4 hours after administration. Five mice were used for each test point. At each test point, whole blood was collected from the mice by cardiac puncture and used to prepare serum samples. Concentrations of the test compounds in serum samples were determined by the paper disc method using *Escherichia coli* CI-304 as the test microorganism.

The results thus obtained are shown in Table 2. For purposes of comparison, the enteral absorbability of ofloxacin and OPC-7241 was tested in the same manner as described above and the results thus obtained are also shown in Table 2.

TABLE 2

| Test compound | Concentration in serum (μg/ml) | | | |
|---|---|---|---|---|
| | 30 min. | 1 hr. | 2 hr. | 4 hr. |
| Compound 3 | 24.2 | 22.4 | 12.6 | 8.4 |
| Compound 9 | 20.2 | 15.9 | 7.7 | 4.5 |
| Compound 11 | 20.8 | 15.8 | 7.2 | 5.3 |
| Compound 15 | 15.0 | 11.7 | 6.7 | 4.3 |
| Compound 16 | 16.4 | 13.6 | 8.1 | 4.8 |
| Compound 25 | 15.5 | 14.9 | 9.3 | 5.4 |
| Compound 29 | 15.6 | 14.4 | 9.8 | 4.2 |
| Compound 31 | 13.8 | 12.7 | 8.4 | 5.0 |
| Compound 35 | 24.5 | 22.0 | 11.8 | 8.5 |
| Compound 38 | 26.7 | 24.1 | 13.5 | 9.0 |
| Ofloxacin | 9.0 | 6.2 | 2.6 | 1.2 |
| OPC-7241 | 9.3 | 7.8 | 4.1 | 2.2 |

As is evident from Table 2, it is noted that the present compounds [I] have much better eteral absorbability and a much longer duration of action than ofloxacin and OPC-7241.

(Therapeutic Effect on Experimentally Induced Infection in Mice)

Using male ddY strain mice infected with *Escherichia coli* CI-304 (in groups of five; weighing 20±1 g), the therapeutic effect of some typical examples of the present compounds [I] was tested. The therapeutic effect was evaluated by administering each test compound orally to infected mice and calculating $ED_{50}$ from the number of mice surviving after the lapse of 7 days. Infected mice were prepared by suspending cells of the aforesaid *Escherichia coli* strain in a 5% mucin solution and injecting this suspension into the peritoneal cavity of mice. The dose of the bacterial cells was ten times the minimal lethal dose which had previously been determined by a preliminary test. One hour after inoculation of the bacterial cells, each test compound was administered orally to the mice.

The results thus obtained are shown in Table 3. For purposes of comparison, ofloxacin and OPC-7241 were tested in the same manner as described above and the results thus obtained are also shown in Table 3.

TABLE 3

| Test compound | Therapeutic effect, $ED_{50}$ (mg/kg) |
|---|---|
| Compound 3 | 0.52 |
| Compound 16 | 0.71 |
| Compound 29 | 0.69 |
| Ofloxacin | 0.90 |
| OPC-7241 | 1.70 |

As is evident from Table 3, it is noted that the present compounds [I] have an excellent therapeutic effect on bacterial infection.

The present invention is further illustrated by the following reference examples and the following examples.

REFERENCE EXAMPLE 1 (PROCEDURE 1 FOR THE PREPARATION OF COMPOUNDS [VI])

(Step g)

86 g (1.00 mole) of β-butyrolactone was added to 146 g (1.00 mole) of 3-chloro-4-fluoroaniline, and this mixture was stirred at 80°–90° C. for 30 minutes and then allowed to cool to room temperature. To the resulting reaction solution was added 1000 ml of ether. This mixture was filtered to remove any insoluble matter, and the filtrate thus obtained was extracted with 750 ml of a 2N aqueous solution of sodium hydroxide. This extract was acidified with 130 ml of concentrated hydrochloric acid and then extracted with 1000 ml of ether. The ether layer was separated, dried over anhydrous sodium sulfate and then evaporated to dryness. Thus, there was obtained 111 g (47.9% yield) of 3-(3-chloro-4-fluoroanilino) butyric acid in the form of pale-yellow oily matter.

(Step h)

400 g of polyphosphoric acid was added to 92.66 g (0.40 mole) of the 3-(3-chloro-4-fluoroanilino) butyric acid and this mixture was stirred at 110° C. for 1.5 hours. After being allowed to cool to room temperature, the resulting reaction solution was diluted with 3 liters of water and then adjusted to pH 4–5 with an aqueous sodium hydroxide solution. Then, the solid matter which separated out was extracted with chloroform and this extract was concentrated under reduced pressure. The residue thus obtained was purified by silica gel column chromatography (using chloroform as the developing solvent). The fraction containing the desired product was evaporated to dryness under reduced pressure and the resulting residue was recrystallized from benzene to obtain 7.43 g (8.7% yield) of 5-chloro-6-fluoro-2-methyl-4-oxo-1,2,3, 4-tetrahydroquinoline in the form of yellow crystals. On the other hand, another fraction was worked up in the same manner as above to obtain 8.55 g (10.0% yield) of a structural isomer thereof, or 7-chloro-6-fluoro-2-methyl-4-oxo-1,2,3,4-tetrahydroquinoline, in the form of yellow crystals.

(Step j)

A mixture of 6.41 g (0.03 mole) of the 5-chloro-6-fluoro-2-methyl-4-oxo-1,2,3,4-tetrahydroquinoline and 6.49 g (0.03 mole) of ethoxymethylenemalonic acid diethyl ester was stirred, in the absence of solvent, at 200°–210° C. for 1.5 hours and then allowed to cool to room temperature. Thus, there was obtained 11.50 g of (5-chloro-6-fluoro-2-methyl-4-oxo-1,2,3,4-tetrahydroquinolin-1-yl) aminomethylene-malonic acid diethyl ester in the form of pale-yellow oily matter.

(Step k)

60 g of polyphosphoric acid was added to 11.50 g (0.03 mole) of the aforesaid (5-chloro-6-fluoro-2-methyl-4-oxo-1,2,3,4-tetrahydroquinolin-1-yl) aminomethylene malonic acid diethyl ester and this mixture was stirred at 110°–120° C. for 30 minutes. After the resulting reaction solution was allowed to cool to room temperature, 500 ml of water was added thereto and the precipitate which separated out was collected by filtration. This precipitate was recrystallized from acetic acid to obtain 8.29 g (81.8% yield) of 8-chloro-9-fluoro-5-methyl-6,7-dihydro-1, 7-dioxo-1H, 5H-benzo[ij]quinolizine-2-carboxylic acid ethyl ester in the form of pale-yellow crystals. These crystals had a melting point of 240°-244° C. (dec.).

The following five compounds were prepared in substantially the same manner as described above, except that each of the aforesaid steps was carried out using the corresponding materials (on the same molar basis as described above) and the reaction conditions (such as reaction temperature, reaction time, reaction solvent, etc.) were suitably modified.

8,9-Difluoro-5-methyl-6,7-dihydro-1,7-dioxo-1H,5H-benzo-[ij]quinolizine-2-carboxylic acid ethyl ester [mp 231°-235° C. (dec.)];

8-Chloro-9-fluoro-5-ethyl-6,7-dihydro-1,7-dioxo-1H, 5H-benzo[ij]quinolizine-2-carboxylic acid ethyl ester;

8,9-Dichloro-5-ethyl-6,7-dihydro-1,7-dioxo-1H,5H-benzo-[ij]quinolizine-2-carboxylic acid n-propyl ester;

8-Chloro-9-fluoro-5-methyl-6,7-dihydro-1,7-dioxo-1H,5H-benzo[ij]quinolizine-2-carboxylic acid methyl ester;

8-Chloro-9-bromo-5-methyl-6,7-dihydro-1,7-dioxo-1H, 5H-benzo[ij]quinolizine-2-carboxylic acid methyl ester.

REFERENCE EXAMPLE 2 (PROCEDURE 2 FOR THE PREPARATION OF COMPOUNDS [VI]

(Step g)

86 g (1.00 mole) of β-butyrolactone was added to 162 g (1.00 mole) of 3,4-dichloroaniline, and this mixture was stirred at 110°-120° C. for 1 hour and then allowed to cool to room temperature. To the resulting reaction solution was added 1000 ml of ether. This mixture was filtered to remove any insoluble matter, and the filtrate thus obtained was extracted with 750 ml of a 2N aqueous solution of sodium hydroxide. This extract was acidified with 130 ml of concentrated hydrochloric acid and then extracted with 1000 ml of ether. The ether layer was separated, dried over anhydrous sodium sulfate and then evaporated to dryness. Thus, there was obtained 128 g (51.6% yield) of 3-(3,4-dichloroanilino)butyric acid in the form of pale-yellow crystals.

(Step h)

300 g of polyphosphoric acid was added to 99.24 g (0.40 mole) of the 3-(3,4-dichloroanilino)butyric acid and this mixture was stirred at 90°-100° C. for 4 hours. After being allowed to cool to room temperature, the resulting reaction solution was diluted with 3 liters of water and then adjusted to pH 4-5 with an aqueous sodium hydroxide solution. Then, the solid matter which separated out was extracted with chloroform and this extract was concentrated under reduced pressure. The residue thus obtained was purified by silica gel column chromatography (using chloroform as the developing solvent). The fraction containing the desired product was evaporated to dryness under reduced pressure and the resulting residue was recrystallized from benzene to obtain 9.94 g (10.8% yield) of 5,6-dichloro-2-methyl-4-oxo-1,2,3,4-tetra-hydroquinoline in the form of yellow crystals. On the other hand, another fraction was worked up in the same manner as above to obtain 13.53 g (14.7% yield) of a structural isomer thereof, or 6,7-dichloro-2-methyl-4-oxo-1,2,3,4-tetrahydroquinoline, in the form of yellow crystals.

(Step j)

A mixture of 6.90 g (0.03 mole) of the 5,6-dichloro-2-methyl-4-oxo-1,2,3,4-tetrahydroquinoline and 6.49 g (0.03 mole) of ethoxymethylenemalonic acid diethyl ester was stirred, in the absence of solvent, at 190°-200° C. for 3 hours and then allowed to cool to room temperature. Thus, there was obtained 12.01 g of (5,6-dichloro-2-methyl-4-oxo-1,2,3,4-tetrahydroquinolin-1-yl) aminomethylenemalonic acid diethyl ester in the form of pale-yellow oily matter.

(Step k)

60 g of polyphosphoric acid was added to 12.01 g (0.03 mole) of the aforesaid 5,6-dichloro-2-methyl-4-oxo-1,2,3,4-tetrahydroquinolin-1-yl) aminomethylenemalonic acid diethyl ester and this mixture was stirred at 110°-120° C. for 20 minutes. After the resulting reaction solution was allowed to cool to room temperature, 500 ml of water was added thereto and the precipitate which separated out was collected by filtration. This precipitate was recrystallized from acetic acid to obtain 9.05 g (85.2% yield) of 8,9-dichloro-5-methyl-6,7-dihydro-1,7-dioxo-1H, 5H-benzo[ij]quinolizine-2-carboxylic acid ethyl ester in the form of pale-yellow crystals. These crystals had a melting point of 234°-237° C. (dec.).

REFERENCE EXAMPLE 3 (PROCEDURE 1 FOR THE PREPARATION OF COMPOUNDS [V]

(Step a)

6.75 g (0.02 mole) of 8-chloro-9-fluoro-5-methyl-6,7-dihydro-1,7-dioxo-1H,5H-benzo[ij]quinolizine-2-carboxylic acid ethyl ester was suspended in 120 ml of chloroform, 6.89 g (0.08 mole) of piperazine was added thereto, and this mixture was stirred at 20°-25° C. for 6 hours. The resulting reaction solution was concentrated under reduced pressure and the residue thus obtained was purified by silica gel column chromatography [using a chloroform-methanol mixture (with a volume ratio of 10.1) as the developing solvent]. The fraction containing the desired product was evaporated to dryness under reduced pressure and the resulting residue was recrystallized from benzene to obtain 4.79 g (61.8% yield) of 9-fluoro-5-methyl-8-(1-piperazinyl)-6,7-dihydro-1,7-dioxo-1H,5H-benzo[ij]quinolizine-2-carboxylic acid ethyl ester in the form of yellow crystals.

The following ten compounds were prepared in substantially the same manner as described above, except that the aforesaid Step a was carried out using the corresponding materials (on the same molar basis as described above) and the reaction conditions (such as reaction temperature, reaction time, reaction solvent, etc.) were suitably modified. These compounds were obtained in the form of yellow crystals or oily matter and their yields were in the range of 58.3 to 86.1%.

9-Chloro-5-methyl-8-(1-piperazinyl)-6,7-dihydro-1,7-dioxo-1H, 5H-benzo[ij]quinolizine-2-carboxylic acid ethyl ester; [mp 197°-200° C.(dec.)];

9-Fluoro-5-methyl-8-(4-methyl-1-piperazinyl)-6,7-dihydro-1,7-dioxo-1H,5H-benzo[]quinolizine-2-carboxylic acid ethyl ester; [mp 247°-250° C.(dec.)];

9-Fluoro-5-methyl-8-(4-ethyl-1-piperazinyl)-6,7-dihydro-1,7-dioxo-1H, 5H-benzo[ij]quinolizine-2-carboxylic acid ethyl ester;

9-Chloro-5-ethyl-8-(1-piperazinyl)-6,7-dihydro-1,7-dioxo-1H, 5H-benzo[ij]quinolizine-2-carboxylic acid n-propyl ester;

9-Fluoro-5-ethyl-8-(4-methyl-1-piperazinyl)-6,7-dihydro-1,7-dioxo-1H, 5H-benzo[ij]quinolizine-2-carboxylic acid ethyl ester;

9-Chloro-5-methyl-8-(4-methyl-1-piperazinyl)-6,7-dihydro-1,7-dioxo-1H,5H-benzo[ij]quinolizine-2-carboxylic acid ethyl ester [mp 230°-233° C.(dec.)];

9-Fluoro-5-methyl-8-(4-n-propyl-1-piperazinyl)-6,7-dihydro-1,7-dioxo-1H,5H-benzo[ij]quinolizine-2-carboxylic acid methyl ester;

9-Fluoro-5-methyl-8-(3,4-dimethyl-1-piperazinyl)-6,7-dihydro-1,7-dioxo-1H,5H-benzo[ij]quinolizine-2-carboxylic acid ethyl ester;

9-Fluoro-5-methyl-8-(3,4,5-trimethyl-1-piperazinyl)-6,7-dihydro-1,7-dioxo-1H,5H-benzo[ij]quinolizine-2-carboxylic acid ethyl ester;

9-Fluoro-5-ethyl-8-(1-piperazinyl)-6,7-dihydro-1,7-dioxo-1H, 5H-benzo[ij]quinolizine-2-carboxylic acid ethyl ester.

REFERENCE EXAMPLE 4 (PROCEDURE 2 FOR THE PREPARATION OF COMPOUNDS [V])

(Step a)

6.43 g (0.02 mole) of 8,9-difluoro-5-methyl-6,7-dihydro-1,7-dioxo-1H,5H-benzo[ij]quinolizine-2-carboxylic acid ethyl ester was suspended in 60 ml of N,N-dimethylformamide, 6.01 g (0.06 mole) of 2-methylpiperazine was added thereto, and this mixture was stirred at 90°-100° C. for 1 hour. The resulting reaction solution was concentrated under reduced pressure, the residue thus obtained was subjected to silica gel column chromatography [using a chloroform-methanol mixture (with a volume ratio of 10:1) as the developing solvent], and the fraction containing the desired product was collected. This fraction was evaporated to dryness under reduced pressure and the resulting residue was recrystallized from benzene to obtain 5.14 g (64.0% yield) of 9-fluoro-5-methyl-8-(3-methyl-1-piperazinyl)-6,7-dihydro-1,7-dioxo-1H,5H-benzo[ij]quinolizine-2-carboxylic acid ethyl ester in the form of yellow crystals.

The following two compounds were prepared in substantially the same manner as described above, except that the aforesaid Step a was carried out using the corresponding materials (on the same molar basis as described above) and the reaction conditions (such as reaction temperature, reaction time, reaction solvent, etc.) were suitably modified. Both of these compounds had a yellow crystalline aspect and their yields were 71.5% and 66.4%, respectively.

9-Fluoro-5-methyl-8-(4-ethyl-2,5-dimethyl-1-piperazinyl)-6,7-dihydro-1,7-dioxo-1H,5H-benzo[ij]quinolizine-2-carboxylic acid ethyl ester;

9-Chloro-5-methyl-8-(3,4,5-trimethyl-1-piperazinyl)-6,7-dihydro-1,7-dioxo-1H,5H-benzo[ij]quinolizine-2-carboxylic acid ethyl ester.

REFERENCE EXAMPLE 5 (PROCEDURE 1 FOR THE PREPARATION OF COMPOUNDS [VII])

(Step a)

16.89 g (0.05 mole) of 8-chloro-9-fluoro-5-methyl-6,7-dihydro-1,7-dioxo-1H,5H-benzo[ij]quinolizine-2-carboxylic acid ethyl ester was suspended in 300 ml of chloroform, 20.03 g (0.20 mole) of N-methylpiperazine was added thereto, and this mixture was stirred at 40°-50° C. for 4 hours. The resulting reaction solution was concentrated under reduced pressure and the residue thus obtained was purified by silica gel column chromatography [using a chloroform-methanol mixture (with a volume ratio of 10:1) as the developing solvent]. The fraction containing the desired product was evaporated to dryness under reduced pressure and the resulting residue was recrystallized from benzene to obtain 12.89 g (64.2% yield) of 9-fluoro-5-methyl-8-(4-methyl-1-piperazinyl)-6,7-dihydro 1,7-dioxo-1H,5H-benzo[ij]-quinolizine-2-carboxylic acid ethyl ester in the form of yellow crystals.

(Step b)

12.04 g (0.03 mole) of the crystals thus obtained were dissolved in 400 ml of methanol, 1.13 g (0.03 mole) of sodium borohydride was added thereto in small portions, and this mixture was stirred at 20°-25° C. for 7 hours. The resulting reaction solution was concentrated under reduced pressure and the residue thus obtained was purified by silica gel column chromatography [using a chloroform-methanol mixture (with a volume ratio of 7:1) as the developing solvent]. The fraction containing the desired product was collected and evaporated to dryness under reduced pressure to obtain 7.32 g (60.5% yield) of 9-fluoro-5-methyl-8-(4-methyl-1-piperazinyl)-7-hydroxy-6,7-dihydro-1-oxo-1H,5H-benzo[ij]-quinolizine-2-carboxylic acid ethyl ester in the form of a pale-yellow crystalline solid.

(Step c)

6.05 g (0.015 mole) of the aforesaid solid was added to 30 g of polyphosphoric acid and this mixture was stirred at 60°-70° C. for 7 hours. After the resulting reaction solution was allowed to cool to room temperature, 200 ml of water was poured thereinto. The resulting solution was neutralized with sodium hydrogen carbonate and then extracted with 400 ml of chloroform. This extract was dried over anhydrous sodium sulfate and then concentrated under reduced pressure to obtain an oily residue. 100 ml of n-hexane was poured into the oily residue and the resulting mixture was shaken to precipitate the desired product. Thus, there was obtained 5.58 g (96.5% yield) of 9-fluoro-5-methyl-8-(4-methyl-1-piperazinyl)-1-oxo-1H, 5H-benzo[ij]quinolizine-2-carboxylic acid ethyl ester in the form of a pale-yellow solid.

The following eleven compounds were prepared in substantially the same manner as described above, except that each of the aforesaid steps was carried out using the corresponding materials (on the same molar basis as described above) and the reaction conditions (such as reaction temperature, reaction time, reaction solvent, etc.) were suitably modified. These compounds were obtained in the form of a pale-yellow solid.

9-Fluoro-5-methyl-8-(1-piperazinyl)-1-oxo-1H,5H-benzo[ij]quinolizine-2-carboxylic acid ethyl ester;

9-Fluoro-5-methyl-8-(4-ethyl-1-piperazinyl)-1-oxo-1H,5H-benzo[ij]quinolizine-2-carboxylic acidic ethyl ester;

9-Chloro-5-methyl-8-(1-piperazinyl)-1-oxo-1H,5H-benzo[ij]quinolizine-2-carboxylic acid ethyl ester;

9-Chloro-5-ethyl-8-(1-piperazinyl)-1-oxo-1H,5H-benzo[ij]quinolizine-2-carboxylic acid n-propyl ester;

9-Chloro-5-methyl-8-(4-methyl-1-piperazinyl)-1-oxo-1H, 5H-benzo[ij]quinolizine-2-carboxylic acid ethyl ester;

9-Fluoro-5-methyl-8-(3,4-dimethyl-1-piperazinyl)-1-oxo-1H,5H-benzo[ij]quinolizine-2-carboxylic acid methyl ester;

9-Fluoro-5-methyl-8-(3,3-dimethyl-1-piperazinyl)-1-oxo-1H,5H-benzo[ij]quinolizine-2-carboxylic acid ethyl ester;

9-Fluoro-5-methyl-8-(3,4,5-trimethyl-1-piperazinyl)-1-oxo-1H,5H-benzo[ij]quinolizine-2-carboxylic acid ethyl ester;

9-Chloro-5-methyl-8-(4-ethyl-3-methyl-1-piperazinyl)-1-oxo-1H,5H-benzo[ij]quinolizine-2-carboxylic acid ethyl ester;

9-Fluoro-5-methyl-8-(3-methyl-1-piperazinyl)-1-oxo-1H, 5H-benzo[ij]quinolizine-2-carboxylic acid ethyl ester;

9-Fluoro-5-methyl-8-(2,5-dimethyl-1-piperazinyl)-1-oxo-1H,5H-benzo[ij]quinolizine-2-carboxylic acid ethyl ester.

REFERENCE EXAMPLE 6 (PROCEDURE 2 FOR THE PREPARATION OF COMPOUNDS [VII])

(Step a)

14.17 g (0.04 mole) of 8,9-dichloro-5-methyl-6,7-dihydro-1,7-dioxo-1H,5H-benzo[ij]quinolizine-2-carboxylic acid ethyl ester was suspended in 250 ml of acetonitrile, 12.02 g (0.12 mole) of 2-methylpiperazine was added thereto, and this mixture was stirred at 50°-60° C. for 3 hours. The resulting reaction solution was concentrated under reduced pressure and the residue thus obtained was purified by silica gel column chromatography [using a chloroform-methanol mixture (with a volume ratio of 10:1) as the developing solvent]. The fraction containing the desired product was evaporated to dryness under reduced pressure and the resulting residue was recrystallized from benzene to obtain 12.75 g (76.3% yield) of 9-chloro-5-methyl-8-(3-methyl-1-piperazinyl)-6,7-dihydro-1,7-dioxo-1H,5H-benzo[ij]-quinolizine-2-carboxylic acid ethyl ester in the form of yellow crystals.

(Step b)

12.54 g (0.030 mole) of the aforesaid crystals were dissolved in 400 ml of ethanol, 0.87 g (0.023 mole) of sodium borohydride was added thereto in small portions, and this mixture was stirred at 20°-2520 C. for 10 hours. The resulting reaction solution was concentrated under reduced pressure and the residue thus obtained was purified by silica gel column chromatography [using a chloroform-methanol mixture (with a volume ratio of 7:1) as the developing solvent]. The fraction containing the desired product was evaporated to dryness under reduced pressure to obtain 4.82 g (38.3% yield) of 9-chloro-5-methyl-8-(3-methyl-1-piperazinyl)-7-hydroxy-6,7-dihydro-1-oxo-1H,5H-benzo[ij]quinolizine-2-carboxylic acid ethyl ester in the form of a pale-yellow crystalline solid.

(Step c)

4.62 g (0.011 mole) of the aforesaid solid was mixed with 40 g of polyphosphoric acid and this mixture was allowed to stand at 20°-25° C. for 26 hours. 300 ml of water was poured into the resulting reaction solution and this mixture was neutralized with sodium hydrogen carbonate. The neutralized solution was extracted with 600 ml of chloroform, and this extract was dried over anhydrous sodium sulfate and then concentrated under reduced pressure to obtain an oily residue. This oily residue was shaken with 60 ml of n-hexane to precipitate the desired product. Thus, there was obtained 4.34 g (98.2% yield) of 9-chloro-5-methyl-8-(3-methyl-1-piperazinyl)-1-oxo-1H,5H-benzo[ij]quinolizine-2-carboxylic acid ethyl ester in the form of a pale-yellow solid.

The following compound was prepared in substantially the same manner as described above, except that each of the aforesaid steps was carried out using the corresponding materials (on the same molar basis as described above) and the reaction conditions (such as reaction temperature, reaction time, reaction solvent, etc.) were suitably modified. This compound had a pale-yellow solid aspect.

9-Fluoro-5-ethyl-8-(3-methyl-1-piperazinyl)-1-oxo-1H,5H-benzo[ij]quinolizine-2-carboxylic acid ethyl ester.

REFERENCE EXAMPLE 7 (PROCEDURE FOR THE PREPARATION OF COMPOUNDS [X])

(Step d)

7.08 g (0.02 mole) of 8,9-dichloro-5-methyl-6,7-dihydro-1,7-dioxo-1H,5H-benzo[ij]quinolizine-2-carboxylic acid ethyl ester was suspended in a mixture of 14 ml of concentrated hydrochloric acid and 56 ml of acetic acid, and this suspension was stirred at 110°-120° C. for 3 hours to hydrolyze the starting material. The resulting reaction solution was allowed to cool to room temperature. The precipitate which separated out was collected by filtration and washed with water to obtain 5.61 g (86.0% yield) of 8,9-dichloro-5-methyl-6,7-dihydro-1,7-dioxo-1H,5H-benzo[ij]quinolizine-2-carboxylic acid in the form of pale-yellow crystals.

The following compound was prepared in substantially the same manner as described above, except that the aforesaid Step d was carried out using the corresponding material [VI] (on the same molar basis as described above) and the reaction conditions (such as reaction temperature, reaction time, reaction solvent, etc.) were suitably modified. This compound had a pale-yellow crystalline aspect and its yield was 65.5%.

8-Chloro-9-fluoro-5-methyl-6,7-dihydro-1,7-dioxo-1H,5H-benzo[ij]quinolizine-2-carboxylic acid [mp 247°-254° C. (dec.)].

REFERENCE EXAMPLE 8 (PROCEDURE FOR THE PREPARATION OF COMPOUNDS [XI])

(Step d)

24.62 g (0.07 mole) of 8-chloro-9-fluoro-5-ethyl-6,7-dihydro-1,7-dioxo-1H,5H-benzo[ij]quinolizine-2-carboxylic acid ethyl ester was suspended in a mixture of 50 ml of concentrated hydrochloric acid and 200 ml of acetic acid, and this suspension was stirred at 110°-120° C. for 3 hours to hydrolyze the starting material. The resulting reaction solution was allowed to cool to room temperature. The precipitate which separated out was collected by filtration and washed with water to obtain 16.95 g (74.8% yield) of 8-chloro-9-fluoro-5-ethyl-6,7-dihydro-1,7-dioxo-1H,5H-benzo[ij]quinolizine-2-carboxylic acid in the form of pale-yellow crystals.

(Step e)

16.18 g (0.05 mole) of the aforesaid crystals were suspended in 500 ml of water, 5.67 g (0.15 mole) of sodium borohydride was added thereto in small portions, and this mixture was stirred at 20°-25° C. for 10 hours. The resulting reaction solution was acidified by the addition of dilute hydrochloric acid. The crystals which separated out were collected by filtration and successively washed with water. These crystals were recrystallized from acetic acid to obtain 8.79 g (54.0% yield) of 8-chloro-9-fluoro-5-ethyl-7-hydroxy-6,7-dihydro-1-oxo-1H,5H-benzo[ij]quinolizine-2-carboxylic acid in the form of pale-yellow crystals.

(Step f)

8.14 g (0.025 mole) of the aforesaid crystals were mixed with 40 g of polyphosphoric acid and this mixture was stirred at 60°-70° C. for 7 hours. 200 ml of water was poured into the resulting reaction solution. The crystals which separated out were collected by filtration and successively washed with water. These crystals were recrystallized from acetic acid to obtain 5.73 g (74.5% yield) of 8-chloro-9-fluoro-5-ethyl-1-oxo-1H, 5H-benzo[ij]quinolizine-2-carboxylic acid in the form of pale-yellow crystals.

The following compound was prepared in substantially the same manner as described above, except that each of the aforesaid steps was carried out using the corresponding materials (on the same molar basis as described above) and the reaction conditions (such as reaction temperature, reaction time, reaction solvent, etc.) were suitably modified. This compound had a pale-yellow crystalline aspect.

8-Chloro-9-fluoro-5-methyl-1-oxo-1H,5H-benzo[ij]quinolizine-2-carboxylic acid.

EXAMPLE 1 (COMPOUND 1)

3.87 g (0.01 mole) of 9-fluoro-5-methyl-8-(1-piperazinyl)-6,7-dihydro-1,7-dioxo-1H,5H-benzo[ij]quinolizine-2-carboxylic acid ethyl ester was suspended in 12 ml of ethanol, 50 ml of a 2N aqueous solution of sodium hydroxide was added thereto, and this mixture was stirred at 20°-25° C. for 2 hours to hydrolyze the starting material. The resulting reaction solution was adjusted to pH 4-5 by the addition of acetic acid under cooling with ice. The precipitate which separated out was collected by filtration and recrystallized from ethanol to obtain 2.91 g (81.0% yield) of 9-fluoro-5-methyl-8-(1-piperazinyl)-6,7-dihydro-1,7-dioxo-1H,5H-benzo[ij]quinolizine-2-carboxylic acid in the form of yellow crystals. These crystals had a melting point of 261°-263° C. (dec.).

Analysis: Calcd. for $C_{18}H_{18}FN_3O_4$(%): C, 60.16; H, 5.05; N, 11.70. Found (%): C, 59.90; H, 4.83; N, 11.43.

Infrared absorption spectrum (cm$^{-1}$; KBr): 1720, 1675, 1620.

$^1$H-Nuclear magnetic resonance spectrum ($\delta$; $CF_3COOD$): 1.86 (3H, d), 3.27-3.70 (2H, m), 3.70-4.50 (8H, m), 5.15-5.60 (1H, m), 8.43 (1H, d), 9.47 (1H, s).

The following compounds of Examples 2 to 8 were prepared in substantially the same manner as described in Example 1 above, except that the 9-fluoro-5-methyl-8-(1-piperazinyl)-6,7-dihydro-1,7-dioxo-1H,5H-benzo[ij]quinolizine-2-carboxylic acid ethyl ester (0.01 mole) was replaced by the corresponding benzo[ij]quinolizine-2-carboxylic acid ester derivative [II], particularly the compound [V], (0.01 mole).

EXAMPLE 2 (COMPOUND 2)

9-Chloro-5-methyl-8-(1-piperazinyl)-6,7-dihydro-1,7-dioxo-1H, 5H-benzo[ij]quinolizine-2-carboxylic acid.

Aspect (Yield): Yellow crystals (3.19 g).

Melting point (dec.): 245°-250° C. (from ethanol).

Analysis: Calcd. for $C_{18}H_{18}CZN_3O_4$ (%): C, 57.52; H, 4.83; N, 11.18. Found (%): C, 57.68; H, 4.66; N, 11.02.

Infrared absorption spectrum (cm$^{-1}$; KBr): 1715, 1670, 1615.

$^1$H-Nuclear magnetic resonance spectrum ($\delta$; $CF_3COOD$): 1.85 (3H, d), 3.25-4.50 (10H, m), 5.17-5.60 (1H, m), 8.83 (1H, s), 9.45 (1H, s).

EXAMPLE 3 (COMPOUND 3)

9-Fluoro-5-methyl-8-(4-methyl-1-piperazinyl)-6, 7-dihydro-1,7-dioxo-1H, 5H-benzo[ij]quinolizine-2-carboxylic acid.

Aspect (Yield): Yellow crystals (2.65 g).

Melting point (dec.): 220°-229° C. (from ethanol).

Analysis: Calcd. for $C_{19}H_{20}FN_3O_4$ (%): C, 61.11; H, 5.40; N, 11.26. Found (%): C, 61.24; H, 5.41; N, 11.17.

Infrared absorption spectrum (cm$^{-1}$; KBr) : 1715, 1665, 1620.

$^1$H-Nuclear magnetic resonance spectrum ($\delta$; $CF_3COOD$): 1.82 (3H, d), 3.23 (3H, s), 3.30-3.77 (2H, m), 3.77-4.50 (8H, m), 5.10-5.70 (1H, m), 8.37 (1H, d), 9.37 (1H, s).

EXAMPLE 4

9-Fluoro-5-methyl-8-(4-ethyl-1-piperazinyl)-6, 7-dihydro-1,7-dioxo-1H, 5H-benzo[ij]quinolizine-2-carboxylic acid.

Aspect (Yield) : Yellow crystals (2.32 g).

Melting point (dec.): 256°-258° C. (from ethanol).

Analysis: Calcd. for $C_{20}H_{22}FN_3O_4$(%): C, 62.00; H, 5.72; N, 10.85. Found (%): C, 62.24; H, 5.81; N, 10.71.

Infrared absorption spectrum (cm$^{-1}$; KBr): 1715, 1670, 1620.

$^1$H-Nuclear magnetic resonance spectrum ($\delta$; $CF_3COOD$): 1.55 (3H, t), 1.83 (3H, d), 3.20-4.50 (12H, m), 5.10-5.65 (1H, m), 8.43 (1H, d), 9.37 (1H, s).

EXAMPLE 5

9-Chloro-5-ethyl-8-(1-piperazinyl)-6, 7-dihydro-1, 7-dioxo-1H, 5H-benzo[ij]quinolizine-2-carboxylic acid.

Aspect (Yield): Yellow crystals (2.56 g).

Melting point (dec.): 255°-260° C. (from ethanol).

Analysis: Calcd. for $C_{19}H_{20}CZN_3O_4$(%): C, 58.54; H, 5.17; N, 10.78. Found (%): C, 58.46; H, 4.98; N, 11.00.

Infrared absorption spectrum (cm$^{-1}$; KBr) : 1720, 1670, 1620.

$^1$H-Nuclear magnetic resonance spectrum ($\delta$; $CF_3COOD$): 1.15 (3H, t), 2.00-2.50 (2H, m), 3.30-4.50 (10H, m), 5.15-5.60 (1H, m), 8.80 (1H, s), 9.44 (1H, s).

EXAMPLE 6 (COMPOUND 6)

9-Fluoro-5-ethyl-8-(4-methyl-1-piperazinyl)-6, 7-dihydro-1,7-dioxo-1H,5H-benzo[ij]quinolizine-2-carboxylic acid.

Aspect (Yield): Yellow crystals (2.15 g).

Melting point (dec.): 230°-237° C. (from ethanol).

Analysis: Calcd. for $C_{20}H_{22}FN_3O_4$(%): C, 62.00: H, 5.72; N, 10.85. Found (%): C, 61.82; H, 6.01; N, 10.73.

Infrared absorption spectrum (cm$^{-1}$; KBr): 1715, 1670, 1620.

$^1$H-Nuclear magnetic resonance spectrum ($\delta$; CF3COOD): 1.10 (3H, t), 2.00-2.50 (2H, m), 3.20 (3H, s), 3.30-4.50 (10H, m), 5.15-5.70 (1H, m), 8.40 (1H, d), 9.40 (1H, s).

EXAMPLE 7 (COMPOUND 7)

9-Chloro-5-methyl-8-(4-methyl-1-piperazinyl)-6, 7-dihydro-1,7-dioxo-1H, 5H-benzo[ij]quinolizine-2-carboxylic acid.

Aspect (Yield): Yellow crystals (3.24 g).
Melting point (dec.): 230°–233° C. (from ethanol).
Analysis: Calcd. for $C_{19}H_{20}CZN_3O_4$(%): C, 58.54; H, 5.17; N, 10.78. Found (%): C, 58.31; H, 4.98; N, 11.01.
Infrared absorption spectrum (cm$^{-1}$; KBr): 1715, 1670, 1615.
$^1$H-Nuclear magnetic resonace spectrum ($\delta$; CF$_3$COOD): 1.83 (3H, d), 3.20 (3H, s), 3.25–4.50 (10H, m), 5.17–5.56 (1H, m), 8.80 (1H, s), 9.40 (1H, s).

EXAMPLE 8 (COMPOUND 8)

9-fluoro-5-methyl-8-(4-n-propyl-1-piperazinyl)-6, 7-dihydro-1,7-dioxo-1H, 5H-benzo[ij]quinolizine-2-carboxylic acid.

Aspect (Yield): Yellow crystals (3.01 g).
Melting point (dec.): 266°–272° C. (from ethanol).
Analysis: Calcd. for $C_{21}H_{24}FN_3O_4$(%): C, 62.83; H, 6.03; N, 10.47. Found (%): C, 63.10; H, 5.98; N, 10.33.
Infrared absorption spectrum (cm$^{-1}$; KBr): 1720, 1665, 1620.
$^1$H-Nuclear magnetic resonance spectrum ($\delta$; CF$_3$COOD): 1.05 (3H, t), 1.85 (3H, d), 1.90–2.50 (2H, m), 3.25–4.30 (12H, m), 5.10-5.70 (1H, M), 8.45 (1H, d), 9.40 (1H, s).

EXAMPLE 9 (COMPOUND 9)

3.26 g (0.01 mole) of 8, 9-dichloro-5-methyl-6, 7-dihydro-1,7-dioxo-1H, 5H-benzo[ij]quinolizine-2-carboxylic acid was suspended in 30 ml of methyl cellosolve, 3.43 g (0.03 mole) of N-ethylpiperazine was added thereto, and this mixture was stirred at 100°–110° C. for 2 hours. The resulting reaction solution was evaporated to dryness under reduced pressure. 30 ml of methanol was added to the resulting residue and this mixture was stirred. The insoluble matter was collected by filtration and recrystallized from ethanol to obtain 3.23 g (80.0% yield) of 9-chloro-5-methyl-8-(4-ethyl-1-piperazinyl)-6,7-dihydro-1, 7-dioxo-1H, 5H-benzo[ij]quinolizine-2-carboxylic acid in the form of yellow crystals. These crystals had a melting point of 295°–298° C. (dec.).

Analysis: Calcd. for $C_{20}H_{22}CZN_3O_4$(%): C, 59.48; H, 5.49; N, 10.41. Found (%): C, 59.24; H, 5.31; N, 10.29.
Infrared absorption spectrum (cm$^{-1}$; KBr): 1720, 1675, 1615.
$^1$H-Nuclear magnetic resonance spectrum ($\delta$; CF$_3$COOD): 1.60 (3H, t), 1.87 (3H, d), 3.20–4.55 (12H, m), 5.15–5.60 (1H, m), 8.90 (1H, s), 9.45 (1H, s).

The following compounds of Examples 10 to 15 were prepared in substantially the same manner as described in Example 9 above, except that the 8,9-dichloro-5-methyl-6,7-dihydro-1,7-dioxo-1H, 5H-benzo[ij]quinolizine-2-carboxylic acid (0.01 mole) and the N-ethylpiperazine (0.03 mole) were replaced by the corresponding carboxylic acid derivative [III], particularly the compound (X) (0.03 mole) and the corresponding piperazine derivative [IV] (0.03 mole), respectively.

EXAMPLE 10

9-Fluoro-5-ethyl-8-(3-methyl-1-piperazinyl)-6, 7-dihydro-1,7-dioxo-1H, 5H-benzo[ij]quinolizine-2-carboxylic acid.

Aspect (Yield): Yellow crystals (2.52 g).
Melting point (dec.): 242°–247° C. (from ethanol).
Analysis: Calcd. for $C_{20}H_{22}FN_3O_4$(%): C, 62.00; H, 5.72; N, 10.85. Found (%): C, 62.35; H, 6.01; N, 10.87.
Infrared absorption spectrum (cm$^{-1}$; KBr): 1715, 1675, 1615.
$^1$H-Nuclear magnetic resonance spectrum ($\delta$; CF$_3$COOD): 1.10 (3H, t), 1.55 (3H, d), 2.00–2.50 (2H, m), 3.20–4.40 (9H, m), 5.20-5.70 (1H, m), 8.45 (1H, d), 9.40 (1H, s).

EXAMPLE 11 (COMPOUND 11)

9-Fluoro-5-methyl-8-(3,5-dimethyl-1-piperazinyl)-6, 7-dihydro-1,7-dioxo-1H, 5H-benzo[ij[quinolizine-2-carboxylic acid.

Aspect (Yield): Yellow crystals (3.10 g).
Melting point (dec.): 243°–247° C. (from ethanol).
Analysis: Calcd. for $C_{20}H_{22}FN_3O_4$(%): C, 62.00; H, 5.72; N, 10.85. Found (%): C, 61.82; H, 5.57; N, 10.57.
Infrared absorption spectrum (cm$^{-1}$; KBr): 1705, 1685, 1620.
$^1$H-Nuclear magnetic resonance spectrum ($\delta$; CF$_3$COOD): 1.30–2.10 (9H, m), 3.25–4.45 (8H, m), 5.10–5.60 (1H, m), 8.39 (1H, d), 9.35 (1H, s).

EXAMPLE 12 (COMPOUND 12)

9-Fluoro-5-methyl-8-(4-(2-hydroxyethyl)-1-piperazinyl)-6,7-dihydro-1, 7-dioxo-1H, 5H-benzo[ij]quinolizine-2-carboxylic acid.

Aspect (Yield): Yellow crystals (1.45 g).
Melting point (dec.): 266°–268° C. (from ethanol).
Analysis: Calcd. for $C_{20}H_{22}FN_3O_5$(%): C, 59.54; H, 5.50; N, 10.42. Found (%): C, 59.22; H, 5.51; N, 10.31.
Infrared absorption spectrum (cm$^{-1}$; KBr): 1720, 1670, 1620.
$^1$H-Nuclear magnetic resonance spectrum ($\delta$; CF$_3$COOD): 1.85 (3H, d), 3.00–4.60 (14H, m), 5.15–5.60 (1H, m), 8.45 (1H, d), 9.55 (1H, s).

EXAMPLE 13

9-Chloro-5-methyl-8-(4-(2-hydroxyethyl)-1-piperazinyl)-6,7-dihydro-1, 7-dioxo-1H, 5H-benzo[ij]quinolizine-2-carboxylic acid.

Aspect (Yield): Yellow crystals (3.02 g).
Melting point (dec.): 292°–293° C. (from ethanol).
Analysis: Calcd. for $C_{20}H_{22}CZN_3O_5$(%): C, 57.21; H, 5.28; N, 10.01. Found (%): C, 56.94; H, 5.17; N, 9.82.
Infrared absorption spectrum (cm$^{-1}$; KBr): 1720, 1670, 1620.
$^1$H-Nuclear magnetic resonance spectrum ($\delta$; CF$_3$COOD): 1.85 (3H, d), 3.00–4.50 (14H, m), 5.15–5.60 (1H, m), 8.86 (1H, s), 9.43 (1H, s).

EXAMPLE 14

9-Fluoro-5-methyl-8-(3,3,4-trimethyl-1-piperazinyl)-6, 7-dihydro-1,7-dioxo-1H, 5H-benzo[ij]quinolizine-2-carboxylic acid.

Aspect (Yield): Yellow crystals (3.01 g).
Melting point (dec.): 233°–239° C. (from ethanol).
Analysis: Calcd. for $C_{21}H_{24}FN_3O_4$(%): C, 62.83; H, 6.03; N, 10.47. Found (%): C, 63.00; H, 5.99; N, 10.18.
Infrared absorption spectrum (cm$^-$; KBr): 1710, 1685, 1615.
$^1$H-Nuclear magnetic resonance spectrum ($\delta$; CF$_3$COOD): 1.35–2.15 (9H, m), 3.20 (3H, s), 3.35–4.40 (8H, m), 5.15–5.60 (1H, m), 8.40 (1H, d), 9.40 (1H, s).

EXAMPLE 15 (COMPOUND 15)

9-Fluoro-5-methyl-8-(3,3-dimethyl-1-piperazinyl)-6, 7-dihydro-1,7-dioxo-1H, 5H-benzo[ij]quinolizine-2-carboxylic acid.

Aspect (Yield) : Yellow crystals (2.63 g)
Melting point (dec.) : 250°–254° C. (from ethanol)
Analysis: Calcd. for $C_{20}H_{22}FN_3O_4$(%): C, 62.00; H, 5.72; N, 10.85. Found (%): C, 61.85; H, 5.68; N, 10.88.
Infrared absorption spectrum (cm$^{-1}$; KBr): 1710, 1680, 1620.
$^1$H-Nuclear magnetic resonance spectrum (δ; CF$_3$COOD): 1.35–2.15 (9H, m), 3.20–4.50 (8H, m), 5.10∝5.65 (1H, m), 8.40 (1H, d), 9.35 (1H, s).

EXAMPLE 16 (COMPOUND 16)

4.01 g (0.01 mole) of 9-fluoro-5-methyl-8-(3-methyl-1-piperazinyl)-6,7-dihydro-1, 7-dioxo-1H, 5H-benzo[ij]-quinolizine-2-carboxylic acid ethyl ester was suspended in a mixture of 20 ml of ethanol and 20 ml of 6N hydrochloric acid, and this suspension was stirred at 80°–90° C. for 5 hours to hydrolyze the starting material. The resulting reaction solution was adjusted to pH 7–8 by the addition of 28% aqueous ammonia under cooling with ice. The precipitate which separated out was collected by filtration and recrystallized from a water-ethanol mixture (with a volume ratio of 1:1) to obtain 2.69 g (72.0% yield) of 9-fluoro-5-methyl-8-(3-methyl-1-piperazinyl)-6,7-dihydro-1, 7-dioxo-1H, 5H-benzo[ij]-quinolizine-2-carboxylic acid in the form of yellow crystals. These crystals had a melting point of 231°–234° C. (dec.) .
Analysis: Calcd. for $C_{19}H_{20}FN_3O_4$(%): C, 61.11; H, 5.40; N, 11.26. Found (%): C, 60.97; H, 5.23; N, 11.21.
Infrared absorption spectrum (cm$^{-1}$; KBr): 1710, 1680, 1620.
$^1$H-Nuclear magnetic resonance spectrum (δ; CF$_3$COOD): 1.40–2.10 (6H, m), 3.25–4.45 (9H, m), 5.15–5.70 (1H, m), 8.40 (1H, d), 9.40 (1H, s).

The following compounds of Examples 17 and 18 were prepared in substantially the same manner as described in Example 16 above, except that the 9-fluoro-5-methyl-8-(3-methyl-1-piperazinyl) -6,7-dihydro-1, 7-dioxo-1H, 5H-benzo[ij]quinolizine-2-carboxylic acid ethyl ester (0.01 mole) was replaced by the corresponding benzo[ij]quinolizine-2-carboxylic acid ester derivative [II], particularly the compound [V], (0.01 mole).

EXAMPLE 17

9-Fluoro-5-methyl-8- (4-ethyl-2, 5-dimethyl-1-piperazinyl) -6,7-dihydro-1, 7-dioxo-1H, 5H-benzo[ij]-quinolizine-2-carboxylic acid.
Aspect (Yield) : Yellow crystals (2.08 g).
Melting point (dec.) : 215°–222° C. (from ethanol).
Analysis: Calcd. for $C_{22}H_{26}FN_3O_4$(%): C, 63.60; H, 6.31; N, 10.12. Found (%): C, 63.78; H, 6.28; N, 10.35.
Infrared absorption spectrum (cm$^{-1}$; KBr) : 1710, 1680, 1615.
1H-Nuclear magnetic resonance spectrum (δ; CF$_3$COOD): 1.20–2.45 (12H, m), 3.20–4.45 (10H, m), 5.20–5.65 (1H, m), 8.75 (1H, d), 9.45 (1H, s).

EXAMPLE 18 (COMPOUND 18)

9-Chloro-5-methyl-8- (3, 4, 5-trimethyl-1-piperazinyl) -6, 7-dihydro-1,7-dioxo-1H, 5H-benzo[ij]quinolizine-2-carboxylic acid.
Aspect (Yield) : Yellow crystals (3.55 g).
Melting point (dec.) : 227°–233° C. (from ethanol).
Analysis: Calcd. for $C_{21}H_{24}CZN_3O_4$(%): C, 60.35; H, 5.79; N, 10.06. Found (%): C, 60.29; H, 5.77; N, 10.10.
Infrared absorption spectrum (cm$^{-1}$, KBr): 1710, 1680, 1620.
$^1$H-Nuclear magnetic resonance spectrum (δ; CF$_3$COOD): 1.25–2.10 (9H, m), 3.20 (3H, s), 3.25–4.50 (8H, m), 5.10–5.60 (1H, m), 8.75 (1H, s), 9.40 (1H, s).

The following compounds were prepared in substantially the same manner as described in above examples.
9-Bromo-5-methyl-8- (4-methyl-1-piperazinyl) -6, 7-dihydro-1,7-dioxo-1H, 5H-benzo[ij]quinolizine-2-carboxylic acid;
9-Fluoro-5-methyl-8- (3, 4-dimethyl-1-piperazinyl) -6, 7-dihydro-1,7-dioxo-1H, 5H-benzo[ij]quinolizine-2-carboxylic acid;
9-Fluoro-5-methyl-8- (3, 5-dimethyl-4-n-propyl-1-piperazinyl) -6,7-dihydro-1, 7-dioxo-1H, 5H-benzo[ij]quinolizine-2-carboxylic acid;
9-Chloro-5-ethyl-8- (3, 4-diethyl-5-methyl-1-piperazinyl) -6, 7-dihydro-1, 7-dioxo-1H, 5H-benzo[ij]quinolizine-2-carboxylic acid;
9-Fluoro-5-methyl-8- (5-ethyl-2-methyl-1-piperazinyl) -6,7-dihydro-1, 7-dioxo-1H, 5H-benzo[ij]quinolizine-2-carboxylic acid;
9-Fluoro-5-methyl-8- [4-(2-hydroxyethyl) -3-methyl-1-piperazinyl]-6,7-dihydro-1, 7-dioxo-1H, 5H-benzo[ij]quinolizine-2-carboxylic acid;
9-Chloro-5-ethyl-8- (3-ethyl-1-piperazinyl) -6, 7-dihydro-1,7-dioxo-1H, 5H-benzo[ij]quinolizine-2-carboxylic acid;
9-Fluoro-5-ethyl-8- (4-isopropyl-1-piperazinyl) -6, 7-dihydro-1,7-dioxo-1H, 5H-benzo[ij]quinolizine-2-carboxylic acid.

EXAMPLE 19 (COMPOUND 19)

To 3.85 g (0.01 mole) of 9-fluoro-5-methyl-8- (4-methyl-1-piperazinyl) -1-oxo-1H, 5H-benzo[ij]quinolizine-2-carboxylic acid ethyl ester was added 50 ml of a 1N aqueous solution of sodium hydroxide. This mixture was stirred at 20°–25° C. for 17 hours to hydrolyze the starting material. The resulting reaction solution was adjusted to pH 6–7 by the addition of 1N hydrochloric acid under cooling with ice. The adjusted solution was concentrated under reduced pressure and the resulting residue was purified by silica gel column chromatography [using a chloroform-methanol mixture (with a volume ratio of 2:1) as the developing solvent]. The fraction containing the desired product was evaporated to dryness under reduced pressure and the resulting residue was recrystallized from ethanol to obtain 2.16 g (60.4% yield) of 9-fluoro-5-methyl-8-(4-methyl-1-piperazinyl) -1-oxo-1H, 5H-benzo[ij]quinolizine-2-carboxylic acid in the form of pale-yellow crystals. These crystals had a melting point of 190°–195° C. (dec.).
Analysis: Calcd. for $C_{19}H_{20}FN_3O_3$(%): C,63.85; H, 5.64; N, 11.76. Found (%): C, 63.59; H, 5.66; N, 11.47.
Infrared absorption spectrum (cm$^{-1}$; KBr): 1715, 1615.
$^1$H-Nuclear magnetic resonance spectrum (δ; CDC$Z_3$—CD$_3$OD): 1.56 (3H, d), 2.75 (3H, s), 3.00–3.70 (8H, m), 5.00–5.35 (1H, m), 6.25 (1H, dd), 6.95 (1H, d), 7.75 (1H, d), 8.70 (1H, s).

The following compounds of Examples 20–30 were prepared in substantially the same manner as described in Example 19 above, except that the 9-fluoro-5-methyl-8-(4-methyl-1-piperazinyl)-1-oxo-1H,5H-benzo[ij]-quinolizine-2-carboxylic acid ethyl ester (0.01 mole) was replaced by the corresponding benzo[ij]quinolizine-2-carboxylic acid ester derivative [II], particularly the compound [VII], (0.01 mole).

EXAMPLE 20 (COMPOUND 20)

9-Fluoro-5-methyl-8-(1-piperazinyl)-1-oxo-1H, 5H-benzo[ij]quinolizine-2-carboxylic acid.

Aspect (Yield): Pale-yellow cyrstals (2.07 g)
Melting point (dec.): 236°–240° C. (from ethanol)
Analysis: Calcd. for $C_{18}H_{18}FN_3O_3$(%): C, 62.96; H, 5.28; N, 12.24. Found (%): C, 62.67; H, 5.17; N, 11.97.
Infrared absorption spectrum (cm$^{-1}$; KBr): 1690, 1620.
$^1$H-Nuclear magnetic resonance spectrum (δ; $CF_3COOD$): 1.80 (3H, d), 3.30–4.30 (8H, m), 5.40–5.80 (1H, m), 6.50 (1H, dd), 7.10 (1H, d), 8.15 (1H, d), 9.31 (1H, s).

EXAMPLE 21

9-Fluoro-5-methyl-8-(4-ethyl-1-piperazinyl)-1-oxo-1H, 5H-benzo[ij]quinolizine-2-carboxylic acid.

Aspect (Yield): Pale-yellow crystals (2.33 g)
Melting point (dec.): 197°–204° C. (from ethanol)
Analysis: Calcd. for $C_{20}H_{22}FN_3O_3$(%): C, 64.67; H, 5.97; N, 11.32 Found (%): C, 64.51; H, 5.98; N, 11.20
Infrared absorption spectrum (cm$^{-1}$; KBr) : 1720, 1615.
$^1$H-Nuclear magnetic resonance spectrum (δ; $CF_3COOD$): 1.55 (3H, t), 1.80 (3H, d), 3.20–4.50 (10H, m), 5.45–5.80 (1H, m), 6.52 (1H, dd), 7.00 (1H d), 8.12 (1H, d), 9.40 (1H, s).

EXAMPLE 22 (COMPOUND 22)

9-Chloro-5-methyl-8-(1-8-(1-piperazinyl)-1-oxo-1H,5H-benzo[ij]quinolizine-2-carboxylic acid.

Aspect (Yield): Pale-yellow crystals (2.66 g)
Melting point (dec.): 200°–210° C. (from ethanol)
Analysis: Calcd. for $C_{18}H_{18}CZN_3O_3$(%): C, 60.08; H, 5.04; N, 11.68 Found (%): C, 60.19; H, 5.14; N, 11.47
Infrared absorption spectrum (cm$^{-1}$; KBr) : 1720, 1615.
$^1$H-Nuclear magnetic resonance spectrum (δ; DMSO-d$_6$): 1.42 (3H, d), 2.70–3.40 (8H, m), 5.15–5.45 (1H, m), 6.30 (1H, dd), 6.87 (1H, d), 7.90 (1H, s), 8.85 (1H, s).

EXAMPLE 23

9-Chloro-5-ethyl-8-(1-piperazinyl)-1-oxo-1H, 5H-benzo[ij]quinolizine-2carboxylic acid.

Aspect (Yield): Pale-yellow crystals (2.79 g)
Melting point (dec.): 186°–190° C. (from ethanol)
Analysis: Calcd. for $C_{19}H_{20}CZN_3O_3$(%): C, 61.04; H, 5.39; N, 11.24 Found (%): C, 61.30; H, 5.44; N, 11.23
Infrared absorption spectrum (cm–; KBr): 1720, 1620.
$^1$H-Nuclear magnetic resonance spectrum (δ; $CF_3COOD$): 1.10 (3H, t), 2.00–2.50 (2H, m), 3.30–4.30 (8H, m), 5.40-5.80 (1H, m), 6.50 (1H, dd), 7.10 (1H, d), 8.50 (1H, s), 9.35 (1H, s).

EXAMPLE 24 (COMPOUND 24)

9-Chloro-5-methyl-8-(4-methyl-1-piperazinyl)-1-oxo-1H,5H-benzo[ij]quinolizine-2-carboxylic acid.

Aspect (Yield): Pale-yellow crystals (2.37 g).
Melting point (dec.): 190°–191° C. (from ethanol).
Analysis: Calcd. for $C_{19}H_{20}CZN_3O_3$(%): C, 61.04; H, 5.39; N, 11.24. Found (%): C, 61.30; H, 5.27; N, 11.01.
Infrared absorption spectrum (cm$^{-1}$;KBr): 1720, 1605.
$^1$H-Nuclear magnetic resonance spectrum (δ; CDCZ$_3$—CD$_3$OD): 1.57 (3H, d), 2.66 (3H, m), 2.85–3.75 (8H, m), 4.92–5.25 (1H, m), 6.15 (1H, dd), 6.95 (1H, d), 8.12 (1H, s), 8.63 (1H, s).

EXAMPLE 25 (COMPOUND 25)

9-Fluoro-5-methyl-8-(3,4-dimethyl-1-piperazinyl)-1-oxo-1H, 5H-benzo[ij]quinolizine-2-carboxylic acid.

Aspect (Yield): Pale-yellow crystals (2.14 g).
Melting point (dec.): 188°–192° C. (from ethanol).
Analysis: Calcd. for $C_{20}H_{22}FN_3O_3$(%): C, 64.67; H, 5.97; N, 11.32. Found (%): C, 64.39; H, 5.68; N, 11.04.
Infrared absorption spectrum (cm$^{-1}$; KBr): 1720, 1615.
$^1$H-Nuclear magnetic resonance spectrum (δ; $CF_3COOD$): 1.55 (3H, d), 1.82 (3H, d), 3.20 (3H, s), 3.30–4.25 (7H, m), 5.40–5.80 (1H, m), 6.45 (1H, dd), 7.10 (1H, d), 8.12 (1H, d),

EXAMPLE 26 (COMPOUND 26)

9-Fluoro-5-methyl-8-(3,3-dimethyl-1-piperazinyl)-1-oxo-1H, 5H-benzo[ij]quinolizine-2-carboxylic acid.

Aspect (Yield): Pale-yellow crystals (2.60 g).
Melting point (dec.): 201°–203° C. (from ethanol).
Analysis: Calcd. for $C_{20}H_{22}FN_3O_3$(%): C, 64.67; H, 5.97; N, 11.32. Found (%): C, 64.90; H, 6.07; N, 11.31.
Infrared absorption spectrum (cm $^{-1}$; KBr): 1725, 1615.
$^1$H-Nuclear magnetic resonance spectrum (δ; $CF_3COOD$): 1.30–2.15 (9H, m), 3.30—4.20 (6H, m), 5.50–5.85 (1H, m), 6.50 (1H, dd), 7.08 (1H, d), 8.15 (1H, d), 9.25 (1H, s).

EXAMPLE 27 (COMPOUND 27)

9-Fluoro-5-methyl-8-(3,4,5-trimethyl-1-piperazinyl)-1-oxo-1H, 5H-benzo[ij]quinolizine-2-carboxylic acid.

Aspect (Yield): Pale-yellow crystals (2.55 g)
Melting point (dec.): 174°–177° C. (from ethanol)
Analysis: Calcd. for $C_{21}H_{24}FN_3O_3$(%): C, 65.44; H, 6.28; N, 10.90. Found (%): C, 65.45; H, 6.01; N, 11.07.
Infrared absorption spectrum (cm$^{-1}$; KBr): 1720, 1620.
$^1$H-Nuclear magnetic resonance spectrum (δ; $CF_3COOD$): 1.25–2.20 (9H, m), 3.20 (3H, s), 3.30–4.40 (6H, m), 5.40–5.80 (1H, m), 6.54 (1H, dd), 7.10 (1H, d), 8.12 (1H, d), 9.20 (1H, s).

EXAMPLE 28

9-Chloro-5-methyl-8-(4-ethyl-3-methyl-1-piperazinyl)-1-oxo-1H, 5H-benzo[ij]quinolizine-2-carboxylic acid.

Aspect (Yield): Pale-yellow crystals (1.98 g).
Melting point (dec.): 179°–184° C. (from ethanol).
Analysis:
Calcd. for $C_{21}H_{24}CZN_3O_3$(%): C, 62.76; H, 6.02; N, 10.46. Found (%): C, 63.00; H, 6.24; N, 10.51.
Infrared absorption spectrum (cm$^{-1}$; KBr): 1720, 1620.
$^1$H-Nuclear magnetic resonance spectrum (δ; $CF_3COOD$): 1.20–2.10 (9H, m), 3.30–4.25 (9H, m), 5.35–5.80 (1H, m), 6.50 (1H, dd), 7.10 (1H, d), 8.49 (1H, s), 9.35 (1H, s).

EXAMPLE 29 (COMPOUND 29)

9-Fluoro-5-methyl-8-(3-methyl-1-piperazinyl)-1-oxo-1H,5H-benzo[ij]quinolizine-2-carboxylic acid.

Aspect (Yield): Pale-yellow crystals (3.06 g).
Melting point (dec.): 205°–210° C. (from ethanol).
Analysis: Calcd. for $C_{19}H_{20}FN_3O_3$(%): C, 63.85; H, 5.64; N, 11.76. Found (%): C, 63.62; H, 5.40; N, 11.70.

Infrared absorption spectrum (cm$^{-1}$, KBr): 1730, 1617.

$^1$H-Nuclear magnetic resonance spectrum ($\delta$; CF$_3$COOD): 1.57 (3H, d), 1.80 (3H, d), 3.35–4.20 (7H, m), 5.45–5.80 (1H, m), 6.50 (1H, dd), 7.05 (1H, d), 8.10 (1H, d), 9.30 (1H, s).

EXAMPLE 30

9-Fluoro-5-methyl-8-(2,5-dimethyl-1-piperazinyl)-1-oxo-1H, 5H-benzo[ij]quinolizine-2-carboxylic acid.

Aspect (Yield): Pale-yellow crystals (1.77 g).
Melting point (dec.): 180°–185° C. (from ethanol).
Analysis: Calcd. for C$_{20}$H$_{22}$FN$_3$O$_3$ (%): C, 64.67; H, 5.97; N, 11.32. Found (%): C, 64.72; H, 6.00; N, 11.28.
Infrared absorption spectrum (cm$^{-1}$; KBr): 1720, 1615.

$^1$H-Nuclear magnetic resonance spectrum ($\delta$; CF$_3$COOD): 1.25–2.12 (9H, m), 3.30–4.40 (6H, m), 5.40–5.80 (1H, m), 6.45 (1H, dd), 7.08 (1H, d), 8.12 (1H, d), 9.33 (1H, s).

EXAMPLE 31 (COMPOUND 31)

To 4.02 g (0.01 mole) of 9-chloro-5-methyl-8-(3-methyl-1-piperazinyl)-1-oxo-1H, 5H-benzo[ij]quinolizine-2-carboxylic acid ethyl ester was added 120 ml of a mixture of 1N aqueous sodium hydroxide and ethanol (with a volume ratio of 5:1). This mixture was stirred at 20°–25° C. for 2 hours to hydrolyze the starting material. The resulting reaction solution was adjusted to pH 6–7 by the addition of 1N hydrochloric acid under cooling with ice. This solution was concentrated under reduced pressure, the resulting residue was purified by silica gel column chromatography [using a chloroform-methanol mixture (with a volume ratio of 2:1) as the developing solvent], and the fraction containing the desired product was collected. This fraction was evaporated to dryness under reduced pressure and the resulting residue was recrystallized from ethanol to obtain 2.89 g (77.3% yield) of 9-chloro-5-methyl-8-(3-methyl-1-piperazinyl)-1-oxo-1H, 5H-benzo[ij]quinolizine-2-carboxylic acid in the form of pale-yellow crystals. These crystals had a melting point of 200°–205° C. (dec.).

Analysis:
Calcd. for C$_{19}$H$_{20}$CZN$_3$O$_3$ (%): C, 61.04; H, 5.39; N, 11.24. Found (%): C, 61.01; H, 5.15; N, 11.07.

Infrared absorption spectrum (cm$^{-1}$; KBr): 1720, 1615.

$^1$H-Nuclear magetic resonance spectrum ($\delta$; CF$_3$COOD): 1.55 (3H, d), 1.82 (3H, d), 3.35–4.30 (7H, m), 5.40–5.80 (1H, m), 6.52 (1H, dd), 7.13 (1H, d), 8.52 (1H, s), 9.33 (1H, s).

The following compound of Example 32 was prepared in substantially the same manner as described in Example 31 above, except that 3.99 g (0.01 mole) of 9-fluoro-5-ethyl-8-(3-methyl-1-piperazinyl)-1-oxo-1H, 5H-benzo[ij]quinolizine-2-carboxylic acid ethyl ester was used.

EXAMPLE 32 (COMPOUND 32)

9-Fluoro-5-ethyl-8-(3-methyl-1-piperazinyl)-1-oxo-1H,5H-benzo[ij]quinolizine-2-carboxylic acid.

Aspect (Yield): Pale-yellow crystals (2.62 g).
Melting point (dec.): 201°–204° C. (from ethanol).
Analysis: Calcd. for C$_{20}$H$_{22}$FN$_3$O$_3$ (%): C, 64.67; H, 5.97; N, 11.32. Found (%): C, 64.73; H, 5.96; N, 11.28.
Infrared absorption spectrum (cm$^{-1}$; KBr): 1725, 1615.

$^1$H-Nuclear magnetic resonance spectrum ($\delta$; CF$_3$COOD): 1.05 (3H, t), 1.55 (3H, d), 2.00–2.50 (2H, m) 3.20–4.35 (7H, m), 5.45–5.80 (1H, m), 6.51 (1H, dd), 7.03 (1H, d), 8.13 (1H, d), 9.28 (1H, s).

EXAMPLE 33

4.62 g (0.015 mole) of 8-chloro-9-fluoro-5-ethyl-1-oxo-1H,5H-benzo[ij]quinolizine-2-carboxylic acid was suspended in 45 ml of dimethyl sulfoxide, 7.69 g (0.06 mole) of N-isopropylpiperazine was added thereto, and this mixture was stirred at 100°–110° C. for 8 hours. The resulting reaction solution was evaporated to dryness under reduced pressure. 40 ml of methanol was added to the resulting residue and this mixture was stirred. The insoluble matter was collected by filtration and recrystallized from ethanol to obtain 3.88 g (64.7% yield) of 9-fluoro-5-ethyl-8-(4-isopropyl-1-piperazinyl)-1-oxo-1H,5H-benzo[ij]quinolizine-2-carboxylic acid in the form of pale-yellow crystals. These crystals had a melting point of 186°–195° C. (dec.).

Analysis: Calcd. for C$_{22}$H$_{26}$FN$_3$O$_3$(%): C, 66.14; H, 6.56; N, 10.52. Found (%): C, 65.85; H, 6.51; N, 10.61.

Infrared absorption spectrum (cm$^{-1}$; KBr): 1720, 1615.

$^1$H-Nuclear magnetic resonance spectrum ($\delta$; CF3COOD): 1.07 (3H, d), 1.65 (6H, d), 2.10 (2H, q), 3.27–4.60 (9H, m), 5.40–5.80 (1H, m), 6.50 (1H, dd), 7.10 (1H, d), 8.10 (1H, d), 9.30 (1H, s).

The following compound of Example 34 was prepared in substantially the same manner as described in Example 33 above, except that 8-chloro-9-fluoro-5-ethyl-1-oxo-1H,5H-benzo[ij]quinolizine-2-carboxylic acid (0.015 mole) and N-isopropylpiperazine (0.06 mole) were replaced by 8-chloro-9-fluoro-5-methyl-1-oxo-1H,5H-benzo[ij]quinolizine-2-carboxylic acid (0.015 mole) and N-(2-hydroxyethyl)piperazine (0.06 mole), respectively.

EXAMPLE 34

9-Fluoro-5-methyl-8-(4-(2-hydroxyethyl)-1-piperazinyl)-1-oxo-1H,5H-benzo[ij]quinolizine-2-carboxylic acid.

Aspect (Yield): Pale-yellow crystals (3.16 g).
Melting point (dec.): 203°–211° C. (from ethanol).
Analysis: Calcd. for C$_{20}$H$_{22}$FN$_3$O$_3$(%): C, 64.67; H, 5.97; N, 11.32. Found (%): C, 64.32; H, 5.88; N, 11.54.
Infrared absorption spectrum (cm$^{-1}$; KBr): 1715, 1615.

$^1$H-Nuclear magnetic resonance spectrum ($\delta$; CF$_3$COOD): 1.80 (3H, d), 3.00–4.60 (12H, m), 5.40–5.80 (1H, m), 6.50 (1H, dd), 7.07 (1H, d), 8.12 (1H, d), 9.30 (1H, s).

The following compounds were prepared in substantially the same manner as described in above examples.

9-Chloro-5-methyl-8-(3,3-dimethyl-1-piperazinyl)-1-oxo-1H,5H-benzo[ij]quinolizine-2-carboxylic acid;

9-Fluoro-5-ethyl-8-(3,4,5-trimethyl-1-piperazinyl)-1-oxo-1H,5H-benzo[ij]quinolizine-2-carboxylic acid;

9-Chloro-5-ethyl-8-(3,4-dimethyl-1-piperazinyl)-1-oxo-1H,5H-benzo[ij]quinolizine-2-carboxylic acid;

9-Fluoro-5-methyl-8-(2,4-dimethyl-1-piperazinyl)-1-oxo-1H,5H-benzo[ij]quinolizine-2-carboxylic acid;

9-Fluoro-5-methyl-8- (3,3,4-trimethyl-1-piperazinyl)-1-oxo-1H, 5H-benzo[ij]quinolizine-2-carboxylic acid;

9-Bromo-5-methyl-8-(3-methyl-1-piperazinyl)-1-oxo-1H, 5H-benzo[ij]quinolizine-2-carboxylic acid.

EXAMPLE 35 (COMPOUND 35)

1.87 g (0.005 mole) of 9-fluoro-5-methyl-8-(4-methyl-1-piperazinyl)-6,7-dihydro-1,7-dioxo-1H,5H-benzo[ij]-quinolizine-2-carboxylic acid was dissolved, at room temperature, in a mixture of 25 ml of 2N aqueous solution of sodium hydroxide and 5 ml of ethanol. This solution was adjusted to pH 1 by the addition of concentrated hydrochloric acid under cooling with ice. The crystals which separated out were collected by filtration and successively washed with small volumes of water and ethanol. These crystals were recrystallized from water to obtain 1.77 g (82.7% yield) of 9-fluoro-5-methyl-8-(4-methyl-1-piperazinyl)-6,7-dihydro-1,7-dioxo-1H,5H-benzo[ij]quinolizine-2-carboxylic acid hydrochloride monohydrate in the form of yellow crystals. These crystals had a melting point of 225°–228° C. (dec.).

Analysis: Calcd. for $C_{19}H_{20}FN_3O_4.HCZ.H_2O$ (%): C, 53.33; H, 5.42; N, 9.82. Found (%): C, 53.50; H, 5.49; N, 9.80.

Infrared absorption spectrum ($cm^{-1}$; KBr): 1730, 1685, 1630.

$^1$H-Nuclear magnetic resonance spectrum ($\delta$; $CF_3COOD$): 1.85 (3H, d), 2.93–4.75 (10H, m), 3.08 (3H, s), 5.07–5.67 (1H, m), 8.43 (1H, d), 9.44 (1H, s).

The following compound of Example 36 was prepared in substantially the same manner as described in Example 35 above, except 1.94 g (0.005 mole) of 9-fluoro-5-ethyl-8-(4-methyl-1-piperazinyl)-6,7-dihydro-1,7-dioxo-1H, 5H-benzo[ij]quinolizine-2-carboxylic acid was used.

EXAMPLE 36

9-Fluoro-5-ethyl-8-(4-methyl-1-piperazinyl)-6,7-dihydro-1,7-dioxo-1H,5H-benzo[ij]quinolizine-2-carboxylic acid hydrochloride monohydrate.

Aspect (Yield): Yellow crystals (1.75 g).

Melting point (dec.): 226°–229° C. (from water).

Analysis: Calcd. for $C_{20}H_{22}FN_3O_4.HCZ.H_2O$ (%): C, 54.36; H, 5.70; N, 9.51. Found (%): C, 54.15; H, 5.74; N, 9.50.

Infrared absorption spectrum ($cm^{-1}$; KBr): 1730, 1680, 1625.

$^1$H-Nuclear magnetic resonance spectrum ($\delta$; $CF_3COOD$): 1.07 (3H, t), 1.83–2.50 (2H, m), 2.97–4.73 (10H, m), 3.28 (3H, s), 4.83–5.40 (1H, m), 8.45 (1H, d), 9.35 (1H, s).

EXAMPLE 37 (COMPOUND 37)

1.79 g (0.005 mole) of 9-fluoro-5-methyl-8-(4-methyl-1-piperazinyl)-1-oxo-1H, 5H-benzo[ij]quinolizine-2-carboxylic acid was dissolved, at room temperature, in a mixture of 17 ml of 3N aqueous solution of sodium hydroxide and 5 ml of isopropanol. This solution was adjusted to pH 1 by the addition of concentrated hydrochloric acid under cooling with ice. The crystals which separated out were collected by filtration and successively washed with small volumes of water and isopropanol. These crystals were recrystallized from water to obtain 1.50 g (76.0% yield) of 9-fluoro-5-methyl-8-(4-methyl-1-piperazinyl)-1-oxo-1H, 5H-benzo[ij]quinolizine-2-carboxylic acid hydrochloride in the form of pale-yellow crystals. These crystals had a melting point of 193°–197° C. (dec.).

Analysis: Calcd. for $C_{19}H_{20}FN_3O_3.HCZ$ (%): C, 57.94; H, 5.37; N, 10.67. Found (%): C, 58.01; H, 5.28; N, 10.49

Infrared absorption spectrum ($cm^{-1}$; KBr): 1725, 1620.

$^1$H-Nuclear magnetic resonance spectrum ($\delta$; $CF_3COOD$): 1.58 (3H, d), 3.20 (3H, s), 3.35–4.30 (8H, m), 5.40–5.80 (1H, m), 6.50 (1H, dd), 7.10 (1H, d), 8.12 (1H, d), 9.31 (1H, s).

The following two compounds were prepared in substantially the same manner as described in Example 37 above.

9-Chloro-5-methyl-8-(1-piperazinyl)-1-oxo-1H, 5H-benzo-[ij]quinolizine-2-carboxylic acid hydrochloride;

9-Fluoro-5-methyl-8-(3-methyl-1-piperazinyl)-1-oxo-1H,5H-benzo[ij]quinolizine-2-carboxylic acid hydrochloride.

EXAMPLE 38 (COMPOUND 38)

2.08 g (0.005 mole) of 9-fluoro-5-methyl-8-(3,4-dimethyl-1-piperazinyl)-6,7-dihydro-1,7-dioxo-1H,5H-benzo-[ij]quinolizine-2-carboxylic acid ethyl ester was suspended in 5 ml of ethanol, 30 ml of a 2N aqueous solution of sodium hydroxide was added thereto, and this mixture was stirred at 15°–20° C. for 3 hours to hydrolyze the starting material. The resulting reaction solution was adjusted to pH 1 by the addition of concentrated hydrochloric acid under cooling with ice. The crystals which separated out were collected by filtration and successively washed with small volumes of water and ethanol. These crystals were recrystallized from water to obtain 1.62 g (73.2% yield) of 9-fluoro-5-methyl-8-(3,4-dimethyl-1-piperazinyl)-6,7-dihydro-1,7-dioxo-1H,5H-benzo[ij]quinolizine-2-carboxylic acid hydrochloride monohydrate in the form of yellow crystals. These crystals had a melting point of 226°–228° C. (dec.).

Analysis: Calcd. for $C_{20}H_{22}FN_3O_4.HCZ.H_2O$ (%): C, 54.36; H, 5.70; N, 9.51 Found (%): C, 54.70; H, 5.38; N, 9.44

Infrared absorption spectrum ($cm^{-1}$; KBr): 1735, 1690, 1625.

$^1$H-Nuclear magnetic resonance spectrum ($\delta$; $CF_3COOD$): 1.67 (3H, d), 1.72 (3H, d), 3.00–4.67 (9H, m), 3.23 (3H, s), 5.17–5.73 (1H, m), 8.43 (1H, d), 9.43 (1H, s).

The following compounds of Examples 39 and 40 were prepared in substantially the same manner as described in Example 38 above, except that 2.15 g (0.005 mole) of 9-fluoro-5-methyl-8-(3,4,5-trimethyl-1-piperazinyl)-6,7-dihydro-1,7-dioxo-1H,5H-benzo[ij]-quinolizine-2-carboxylic acid ethyl ester and 2.01 g (0.005 mole) of 9-fluoro-5-ethyl-8-(1-piperazinyl)-6,7-dihydro-1,7-dioxo-1H,5H-benzo[ij]quinolizine-2-carboxylic acid ethyl ester were used, respectively.

EXAMPLE 39 (COMPOUND 39)

9-Fluoro-5-methyl-8-(3,4,5-trimethyl-1-piperazinyl)-6,7-dihydro-1,7-dioxo-1H,5H-benzo[ij[quinolizine-2-carboxylic acid hydrochloride monohydrate.

Aspect (Yield): Yellow crystals (1.55 g)

Melting point (dec.): 251°–252° C. (from water).

Analysis: Calcd. for $C_{21}H_{24}FN_3O_4.HCZ.H_2O$ (%): C, 55.32; H, 5.97; N, 9.22. Found (%): C, 55.51; H, 5.56; N, 9.09.

Infrared absorption spectrum ($cm^{-1}$; KBr): 1720, 1690, 1625.

$^1$H-Nuclear magnetic resonance spectrum ($\delta$; $CF_3COOD$): 1.43–1.73 (6H, m), 1.85 (3H, d), 2.92–4.53 (8H, m), 3.25 (3H, s), 5.07–5.60 (1H, m), 8.42 (1H, d), 9.42 (1H, s).

EXAMPLE 40

9-Fluoro-5-ethyl-8-(1-piperazinyl)-6,7-dihydro-1,7-dioxo-1H, 5H-benzo[ij]quinolizine-2-carboxylic acid hydrochloride.

Aspect (Yield): Yellow crystals (1.37 g).

Melting point (dec.): 271°14 273° C. (from water).

Analysis: Calcd. for $C_{19}H_{20}FN_3O_4 \cdot HCl$ (%): C, 55.68; H, 5.16; N, 10.26. Found (%): C, 55.56; H, 5.18; N, 10.10.

Infrared absorption spectrum ($cm^{-1}$; KBr): 1730, 1685, 1620.

$^1$H-Nuclear magnetic resonance spectrum ($\delta$; $CF_3COOD$): 1.11 (3H, t), 1.83–2.47 (2H, m), 3.07–4.73 (10H, m), 4.85–5.38 (1H, m), 8.40 (1H, d), 9.32 (1H, s).

What is claimed is:

1. A benzo[ij]quinolizine-2-carboxylic acid of the following formula:

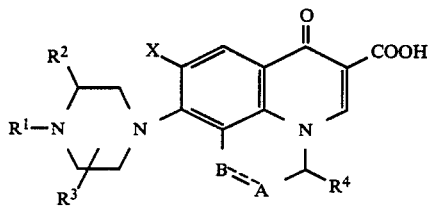

Wherein

A is a methylene group and B is a carbonyl group when A and B are linked by a single bond, or A and B unite together to form a vinylene group when A and B are linked by a double bond, $R^1$ is a hydrogen atom, an alkyl group of 1 to 3 carbon atoms or a 2-hydroxyethyl group, $R^2$ and $R^3$ are hydrogen atoms, methyl groups or ethyl groups and may be identical to or different from each other, $R^3$ may be attached to the same carbon atom as $R^2$, $R^4$ is a methyl or ethyl group, and X is a halogen atom;

or a physiologically acceptable salt thereof, or a hydrate of the compound or the salt.

2. A benzo[ij]quinolizine-2-carboxylic acid derivative as claimed in claim 1 of the following general formula:

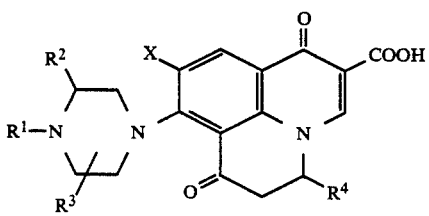

Wherein $R^1$ is hydrogen, methyl, ethyl, n-propyl or 2-hydroxyethyl, $R^2$ is hydrogen or methyl, $R^3$ is hydrogen or methyl and may be attached to the same carbon atom as $R^2$, $R^4$ is methyl or ethyl, and X is fluorine or chlorine;

or a hydrate of a physiologically acceptable salt thereof.

3. A benzo[ij]quinolizine-2-carboxylic acid derivative as claimed in claim 1 of the following general formula:

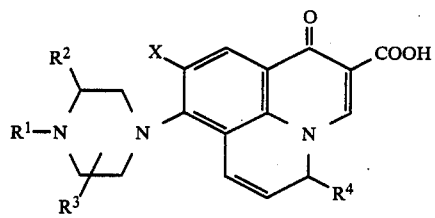

Wherein $R^1$ is hydrogen or methyl, $R^2$ is hydrogen or methyl, $R^3$ is hydrogen or methyl and may be attached to the same carbon atom as $R^2$, $R^4$ is methyl or ethyl, and X is fluorine or chlorine;

or a physiologically acceptable salt thereof.

4. 9-Fluoro-5-methyl-8-(4-methyl-1-piperazinyl)-6,7-dihydro-1,7-dioxo-1H,5H-benzo[ij]quinolizine-2-carboxylic acid.

5. 9-Chloro-5-methyl-8-(4-ethyl-1-piperazinyl)-6,7-dihydro-1,7-dioxo-1H,5H-benzo[ij]quinolizine-2-carboxylic acid.

6. 9-Fluoro-5-methyl-8-(3,5-dimethyl-1-piperazinyl)-6,7-dihydro-1,7-dioxo-1H,5H-benzo[ij]quinolizine-2-carboxylic acid.

7. 9-Fluoro-5-methyl-8-(3,3-dimethyl-1-piperazinyl)-6,7-dihydro-1,7-dioxo-1H,5H-benzo[ij]quinolizine-2-carboxylic acid.

8. 9-Fluoro-5-methyl-8-(3-methyl-1-piperazinyl)-6,7-dihydro-1,7-dioxo-1H,5H-benzo[ij]quinolizine-2-carboxylic acid.

9. 9-Fluoro-5-methyl-8-(3,4-dimethyl-1-piperazinyl)-1-oxo-1H,5H-benzo[ij]quinolizine-2-carboxylic acid.

10. 9-Fluoro-5-methyl-8-(3-methyl-1-piperazinyl)-1-oxo-1H,5H-benzo[ij]W quinolizine-2-carboxylic acid.

11. 9-Chloro-5-methyl-8-(3-methyl-1-piperazinyl)-1-oxo-1H,5H-benzo[]quinolizine-2-carboxylic acid.

12. 9-Fluoro-5-methyl-8-(4-methyl-1-piperazinyl)-6,7-dihydro-1,7-dioxo-1H,5H-benzo[]quinolizine-2-carboxylic acid hydrochloride monohydrate.

13. 9-Fluoro-5-methyl-8-(3,4-dimethyl-1-piperazinyl)-6,7-dihydro-1,7-dioxo-1H,5H-benzo[]quinolizine-2-carboxylic acid hydrochloride monohydrate.

14. A compound of claim 1 wherein A is a methylene group and B is a carbonyl group, and A and B are linked by a single bond.

15. A compound of claim 14 wherein X is flourine or chlorine.

16. A compound of claim 1 wherein A and B are united together to form a vinylene group in which A and B are linked by a double bond.

17. A compound of claim 16 wherein X is flourine or chlorine.

18. Method of using a compound or salt or hydrate of claim 1 for treating bacterial infection in a living subject which comprises administering to such a subject a therepeutically effective amount of such derivative or salt or hydrate of claim 1.

19. Method of claim 18 wherein the administering is carried out by oral administration.

* * * * *